(12) United States Patent
Ino et al.

(10) Patent No.: US 11,518,979 B2
(45) Date of Patent: Dec. 6, 2022

(54) CELL POPULATION COMPRISING ADHERENT CELLS DERIVED FROM FETAL APPENDAGE, METHOD FOR PRODUCING THE SAME, AND PHARMACEUTICAL COMPOSITION

(71) Applicant: KANEKA CORPORATION, Osaka (JP)

(72) Inventors: Keita Ino, Kobe (JP); Yuta Kita, Kobe (JP)

(73) Assignee: KANEKA CORPORATION, Osaka (JP)

( * ) Notice: Subject to any disclaimer, the term of this patent is extended or adjusted under 35 U.S.C. 154(b) by 310 days.

(21) Appl. No.: 16/575,032

(22) Filed: Sep. 18, 2019

(65) Prior Publication Data
US 2020/0032205 A1  Jan. 30, 2020

Related U.S. Application Data

(63) Continuation-in-part of application No. PCT/JP2018/014323, filed on Apr. 3, 2018.

(30) Foreign Application Priority Data

Apr. 3, 2017  (JP) .............................. JP2017-073981

(51) Int. Cl.
| C12N 5/073 | (2010.01) |
| A61K 35/50 | (2015.01) |
| A61K 35/51 | (2015.01) |
| A61K 9/00 | (2006.01) |
| A61K 9/70 | (2006.01) |

(52) U.S. Cl.
CPC .......... *C12N 5/0605* (2013.01); *A61K 9/0019* (2013.01); *A61K 9/70* (2013.01); *A61K 35/50* (2013.01); *A61K 35/51* (2013.01); *C12N 2509/00* (2013.01)

(58) Field of Classification Search
CPC .. C12N 5/0605; C12N 2509/00; A61K 35/50; A61K 35/51
See application file for complete search history.

(56) References Cited

U.S. PATENT DOCUMENTS

2016/0228474 A1* 8/2016 Yamahara ............... A61P 29/00
2020/0360444 A1  11/2020 Ino et al.

FOREIGN PATENT DOCUMENTS

| EP | 3 037 523 A1 | 6/2016 |
| EP | 3 369 810 A1 | 9/2018 |
| EP | 3 608 400 A1 | 2/2020 |
| JP | 2015-61520 A | 4/2015 |
| WO | WO 2013/077428 A1 | 5/2013 |
| WO | WO 2018/186421 A1 | 10/2018 |
| WO | WO 2019/132025 A1 | 7/2019 |

OTHER PUBLICATIONS

Kita et al. Isolation and Characterization of Mesenchymal Stem Cells From the Sub-Amniotic Human Umbilical Cord Lining Membrane. Stem Cells and Development vol. 19, No. 4, p. 493-501 (Year: 2010).*
International Search Report for PCT/JP2018/014323 (PCT/ISA/210) dated Jul. 3, 2018.
Wegmeyer et al., "Mesenchymal Stromal Cell Characteristics Vary Depending on Their Origin", Stem Cells and Development, May 15, 2013, vol. 22, No. 19, pp. 2606-2618, Supplementary Data, total of 63 pages.
Written Opinion of the International Searching Authority for PCT/JP2018/014323 (PCT/ISA/237) dated Jul. 3, 2018.
Batsali et al., "Differential expression of cell cycle and WNT pathway-related genes accounts for differences in the growth and differentiation potential of Wharton's jelly and bone marrow-derived mesenchymal stem cells," Stem Cell Research & Therapy (2017), vol. 8, No. 102, 17 pages.
Extended European Search Report dated Dec. 16, 2020, in European Patent Application No. 18781652.5.
Higuchi et al,. "Stemness of Human Wharton's Jelly Mesenchymal Cells is Maintained by Floating Cultivation," Cellular Reprogramming (2012), vol. 14, No. 5, pp. 448-455.
Jeong et al., "Thrombospondin-2 Secreted by Human Umbilical Cord Blood-Derived Mesenchymal Stem Cells Promotes Chondrogenic Differentiation," Stem Ceils (2013), vol. 31, pp. 2136-2148.

* cited by examiner

*Primary Examiner* — Taeyoon Kim
(74) *Attorney, Agent, or Firm* — Birch, Stewart, Kolasch & Birch, LLP

(57) ABSTRACT

An object of the present invention is to provide a cell population comprising adherent cells having low differentiation capacity derived from a fetal appendage, methods for producing or using the same, and a pharmaceutical composition comprising the cell population, in particular wherein the proportion of CD73- and CD90-positive adherent cells derived from a fetal appendage is 90% or more; and the cell population satisfies a relative expression level of LFA-3 gene to the expression level of SDHA gene of 1.0 or more, in particular wherein the relative expression level of HAPLN1 gene to the expression level of SDHA gene is 4.0 or more and/or the relative expression level of CCND2 gene to the expression level of SDHA gene is 1.5 or less, in particular wherein the proportion of the STRO-1-negative adherent cells derived from a fetal appendage is 95% or more.

4 Claims, 8 Drawing Sheets

CELL POPULATION COMPRISING ADHERENT CELLS DERIVED FROM FETAL APPENDAGE, METHOD FOR PRODUCING THE SAME, AND PHARMACEUTICAL COMPOSITION

CROSS REFERENCE TO RELATED APPLICATIONS

This application is a Continuation-in-Part of PCT International Application No. PCT/JP2018/014323, filed on Apr. 3, 2018, which claims priority under 35 U.S.C. 119(a) to Patent Application No. 2017-073981, filed in Japan on Apr. 3, 2017, all of which are hereby expressly incorporated by reference into the present application.

TECHNICAL FIELD

The present invention relates to a method for producing a cell population comprising adherent cells derived from a fetal appendage. Furthermore, the present invention relates to a cell population comprising adherent cells derived from a fetal appendage and a pharmaceutical composition comprising the cell population.

BACKGROUND ART

It has been reported that adherent cells derived from a fetal appendage (adherent cells derived from a fetal appendage) have the ability to secrete cytokines involved in immunosuppression and thus intravenous administration of a cell suspension containing adherent cells derived from a fetal appendage may treat immune-related diseases and inflammatory diseases. In addition, the fetal appendages as cell sources, such as the placenta, umbilical cord, and fetal membrane, are medical wastes at the time of delivery. Therefore, adherent cells derived from a fetal appendage can be collected noninvasively and expected to be applied to cell therapies for various immune-related diseases and inflammatory diseases.

Patent Document 1 describes a method for producing adherent cells derived from a fetal appendage, a method for cryopreserving adherent cells derived from a fetal appendage, and a therapeutic agent. Particularly, this document states that a mixture comprising adherent cells derived from a fetal appendage is cryopreserved in a solution containing 5 to 10% by mass of dimethyl sulfoxide and containing 5 to 10% by mass of hydroxyethyl starch or 1 to 5% by mass of dextran such that the cryopreserved adherent cells derived from a fetal appendage can be produced as a cell preparation optimized for transplantation.

Patent Document 2 describes a method for preparing a cell population of adherent cells derived from a fetal appendage, comprising the steps of: (D) collecting a cell population of adherent cells derived from a fetal appendage from the amnion of a mammal; (E) inoculating the collected cell population at a cell concentration of 400 to 35000 cells/cm$^2$, followed by initial culture for 2 to 3 days; (F) inoculating the cultured cells at 1/5000 or more and less than 1/10 of the cell concentration of the initial culture, and repeating subculture three or four times with medium replacement twice a week; and (G) maintaining the culture of the cells in the same culture dish until confluent when a colony of cells having a fusiform form is formed in the subculture.

PRIOR ART DOCUMENTS

Patent Documents

Patent Document 1: JP Patent Publication (Kokai) No. 2015-61520 A (2015)
Patent Document 2: International Publication No. WO2013/077428

SUMMARY OF INVENTION

Object to be Solved by the Invention

In recent years, adherent cells derived from a fetal appendage have been found to be a heterogeneous cell population including various cells varying in differentiation capacity, proliferative capacity and cytokine production capacity. For producing a cell preparation with stable quality, it is necessary to prepare a purified, highly homogeneous cell population. In addition, it has been pointed out that ectopic tissue formation may occur when cells capable of differentiating into adipocytes, chondrocytes, and the like are administered in vivo as a cell preparation. For reducing the risk of ectopic tissue formation and improving the safety as a cell preparation, it is desirable to selectively obtain only cells with lower differentiation capacity and prepare the cells as a cell preparation.

Patent Document 1 states that a mixture comprising adherent cells derived from a fetal appendage is cryopreserved in a particular cryopreservation solution such that decrease in the survival rate of adherent cells derived from a fetal appendage after thawing can be prevented, and the cryopreserved adherent cells derived from a fetal appendage can be produced as a cell preparation optimized for transplantation. However, this document makes no mention about the selective preparation of cells having a particular excellent characteristic from among adherent cells derived from a fetal appendage, specifically, the selective preparation of a cell population rich in adherent cells having low differentiation capacity derived from a fetal appendage by utilizing the characteristics of adherent cells derived from a fetal appendage as an index. In Patent Document 2, adherent cells derived from a fetal appendage having high proliferative capacity and differentiation capacity is prepared by inoculating cells at a low density. However, this document neither describes nor suggests the preparation of a cell population rich in adherent cells derived from a fetal appendage having low differentiation capacity utilizing the characteristics of cells contained in the population of adherent cells derived from a fetal appendage as an index.

An object of the present invention is to provide a cell population comprising adherent cells having low differentiation capacity derived from a fetal appendage, a method for producing the same, and a pharmaceutical composition comprising the cell population.

Means for Solving the Object

As a result of intensive studies in order to achieve the above objects, the present inventors found that the adherent cells derived from a fetal appendage which are positive for CD73 and CD90 and in which the LFA-3 gene is highly expressed are included in the cell population comprising adherent cells derived from a fetal appendage, and also found that the cell population comprising adherent cells derived from a fetal appendage having the above cell characteristics has low differentiation capacity. The present invention has been completed on the basis of these findings.

Specifically, the present specification provides the following aspects of the invention:

[1] A method for producing a cell population comprising adherent cells derived from a fetal appendage, the method comprising obtaining a cell population having the following cell characteristics (a) and (b):
(a) in the cell population, the proportion of CD73- and CD90-positive adherent cells derived from a fetal appendage is 90% or more; and
(b) the cell population satisfies a relative expression level of LFA-3 gene to the expression level of SDHA gene of 1.0 or more.

[1-A] A method for producing a cell population comprising adherent cells derived from a fetal appendage, the method comprising obtaining a cell population having the following cell characteristics (a) and (b):
(a) in the cell population, the proportion of CD73- and CD90-positive adherent cells derived from a fetal appendage is 90% or more; and
(b) the cell population satisfies a relative expression level of CCND2 gene to the expression level of SDHA gene of 1.5 or less.

In the following description, when represented as [1], both [1] and [1-A] are included.

[2] A cell population comprising adherent cells derived from a fetal appendage, the cell population having the following cell characteristics (a) and (b):
(a) in the cell population, the proportion of CD73- and CD90-positive adherent cells derived from a fetal appendage is 90% or more; and
(b) in the cell population, the relative expression level of LFA-3 gene to the expression level of SDHA gene is 1.0 or more.

[3] The cell population according to [2], wherein in the cell population, the relative expression level of HAPLN1 gene to the expression level of SDHA gene is 4.0 or more and/or the relative expression level of CCND2 gene to the expression level of SDHA gene is 1.5 or less.

[4] The cell population according to [2] or [3], wherein in the cell population, the proportion of the STRO-1-negative adherent cells derived from a fetal appendage is 95% or more.

[2-A] A cell population comprising adherent cells derived from a fetal appendage, the cell population having the following cell characteristics (a) and (b):
(a) in the cell population, the proportion of CD73- and CD90-positive adherent cells derived from a fetal appendage is 90% or more; and
(b) the cell population satisfies a relative expression level of CCND2 gene to the expression level of SDHA gene of 1.5 or less.

In the following description, when represented as [2], both [2] and [2-A] are included.

[5] A pharmaceutical composition comprising the cell population according to any one of [2] to [4] and a pharmaceutically acceptable vehicle.

[6] The pharmaceutical composition according to [5], wherein a single dose of the adherent cells derived from a fetal appendage to a human is $10^9$ cells/kg body weight or less.

[7] The pharmaceutical composition according to [5] or [6], wherein the pharmaceutical composition is an injectable preparation.

[8] The pharmaceutical composition according to [5] or [6], wherein the pharmaceutical composition is an implantable preparation having a cell aggregate or sheet-like structure.

[9] The pharmaceutical composition according to any one of [5] to [8], wherein the pharmaceutical composition is a therapeutic agent for a disease selected from immunological diseases, ischemic diseases, lower-limb ischemia, cerebrovascular ischemia, kidney ischemia, lung ischemia, neurological diseases, graft-versus-host disease, inflammatory bowel disease, Crohn's disease, ulcerous colitis, radiation enteritis, systemic lupus erythematosus, lupus erythematosus, collagen disease, stroke, cerebral infarction, intracerebral hematoma, cerebrovascular paralysis, liver cirrhosis, atopic dermatitis, multiple sclerosis, psoriasis, epidermolysis bullosa, diabetes mellitus, mycosis fungoides, scleroderma, inflammatory arthritis, rheumatoid arthritis, eye diseases, angiogenesis-related diseases, ischemic heart disease, coronary heart disease, myocardial infarction, angina pectoris, cardiac failure, cardiomyopathy, valvular disease, wound, epithelial damage, fibrosis, lung diseases, and cancers.

[10] A cell population obtained by the production method according to [1].

[11] A use of the cell population according to any one of [2] to [4] for the production of a pharmaceutical composition.

[12] The use according to [11], wherein the pharmaceutical composition is a pharmaceutical composition where a single dose of the adherent cells derived from a fetal appendage to a human is $10^9$ cells/kg body weight or less.

[13] The use according to [11] or [12], wherein the pharmaceutical composition is an injectable preparation.

[14] The use according to [11] or [12], wherein the pharmaceutical composition is an implantable preparation having a cell aggregate or sheet-like structure.

[15] The use according to any one of [11] to [14], wherein the pharmaceutical composition is a therapeutic agent for a disease selected from immunological diseases, ischemic diseases, lower-limb ischemia, neurological diseases, graft-versus-host disease, inflammatory bowel diseases. Crohn's disease, ulcerous colitis, radiation enteritis, systemic lupus erythematosus, lupus erythematosus, collagen disease, stroke, cerebral infarction, intracerebral hematoma, cerebrovascular paralysis, liver cirrhosis, atopic dermatitis, multiple sclerosis, psoriasis, epidermolysis bullosa, diabetes mellitus, mycosis fungoides, scleroderma, inflammatory arthritis, rheumatoid arthritis, eye diseases, angiogenesis-related diseases, ischemic heart disease, coronary heart disease, myocardial infarction, angina pectoris, cardiac failure, cardiomyopathy, valvular disease, wound, epithelial damage, fibrosis, lung diseases, and cancers.

[16] The cell population according to any one of [2] to [4] for use in the treatment of a disease.

[17] The cell population according to [16], wherein a single dose of the adherent cells derived from a fetal appendage to a human is $10^9$ cells/kg body weight or less.

[18] The cell population according to [16] or [17], wherein the cell population is an injectable preparation.

[19] The cell population according to [16] or [17], wherein the cell population is an implantable preparation having a cell aggregate or sheet-like structure.

[20] The cell population according to any one of [16] to [19], wherein the disease is a disease selected from immunological diseases, ischemic diseases, lower-limb ischemia, cerebrovascular ischemia, kidney ischemia, lung ischemia, neurological diseases, graft-versus-host disease, inflammatory bowel disease, Crohn's disease, ulcerous colitis, radiation enteritis, systemic lupus erythematosus, lupus erythematosus, collagen disease, stroke, cerebral infarction, intracerebral hematoma, cerebrovascular paralysis, liver cirrhosis, atopic dermatitis, multiple sclerosis, psoriasis, epidermolysis bullosa, diabetes mellitus, mycosis fungoides, scleroderma, inflammatory arthritis, rheumatoid arthritis, eye diseases, angiogenesis-related diseases, ischemic heart disease, coronary heart disease, myocardial infarction, angina pectoris, cardiac failure, cardiomyopathy, valvular disease, wound, epithelial damage, fibrosis, lung diseases, and cancers.

[21] A method for treating a disease, comprising administering the cell population according to any one of [2] to [4] to a patient in need of treatment.

[22] The method for treating a disease according to [21], wherein a single dose of the adherent cells derived from a fetal appendage to a human is $10^9$ cells/kg body weight or less.

[23] The method for treating a disease according to [21] or [22], wherein the cell population is an injectable preparation.

[24] The method for treating a disease according to [21] or [22], wherein the cell population is an implantable preparation having a cell aggregate or sheet-like structure.

[25] The method for treating a disease according to any one of [21] to [24], wherein the disease is a disease selected from immunological diseases, ischemic diseases, lower-limb ischemia, cerebrovascular ischemia, kidney ischemia, lung ischemia, neurological diseases, graft-versus-host disease, inflammatory bowel disease, Crohn's disease, ulcerous colitis, radiation enteritis, systemic lupus erythematosus, lupus erythematosus, collagen disease, stroke, cerebral infarction, intracerebral hematoma, cerebrovascular paralysis, liver cirrhosis, atopic dermatitis, multiple sclerosis, psoriasis, epidermolysis bullosa, diabetes mellitus, mycosis fungoides, scleroderma, inflammatory arthritis, rheumatoid arthritis, eye diseases, angiogenesis-related diseases, ischemic heart disease, coronary heart disease, myocardial infarction, angina pectoris, cardiac failure, cardiomyopathy, valvular disease, wound, epithelial damage, fibrosis, lung diseases, and cancers.

[26] A composition comprising the cell population according to any one of [2] to [4] and a vehicle.

Advantageous Effects of Invention

According to the present invention, a cell population comprising adherent cells having low differentiation capacity derived from a fetal appendage can be obtained using the positive rate of surface antigens CD73 and CD90 and the expression level of LFA-3 gene as indexes. The cell population has low differentiation capacity and hardly cause ectopic tissue formation in vivo. Thus, the cell population is considered to have high safety. Specifically, for example, it can be used as a pharmaceutical composition for the treatment of immunological diseases, ischemic diseases, heart failure, stroke, fibrosis, and the like.

EMBODIMENT OF CARRYING OUT THE INVENTION

Figure 1:
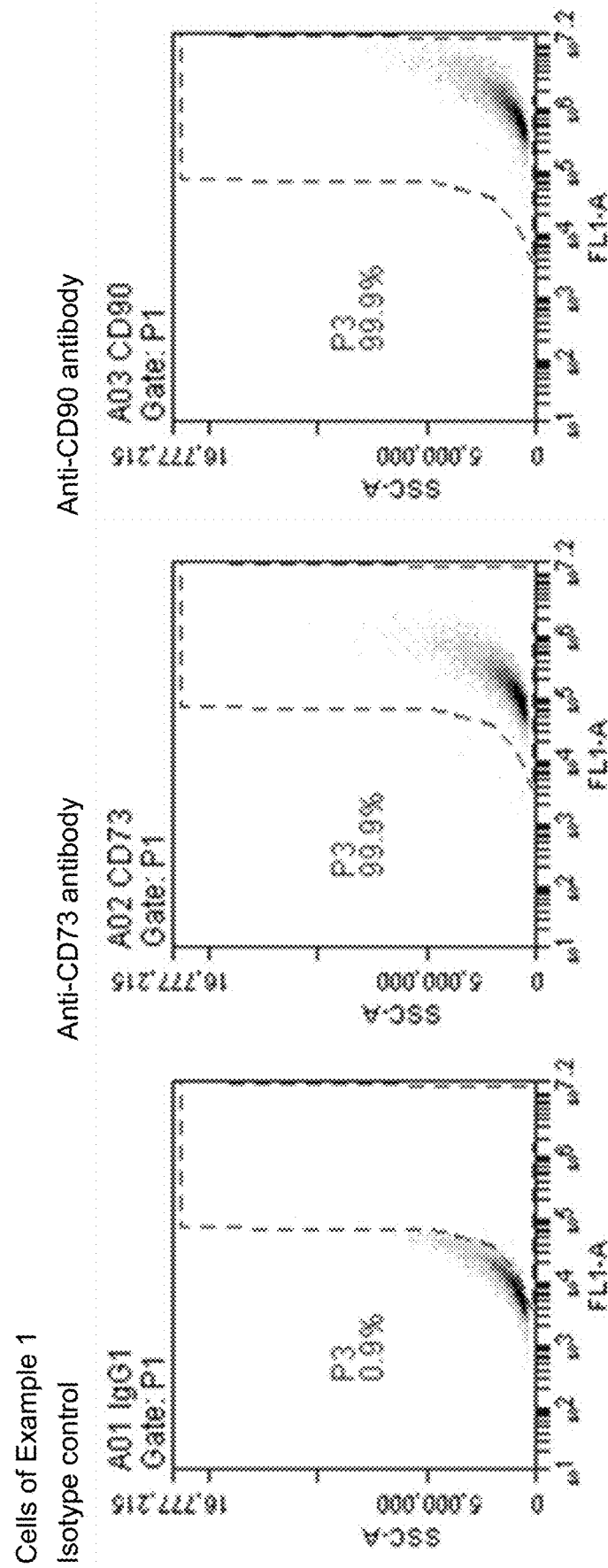
FIG. 1 shows the results of measurement of the proportion of cells positive for CD73 and CD90 using a flow cytometer as to adherent cells derived from a fetal appendage cultured in Example 1.
Figure 2:
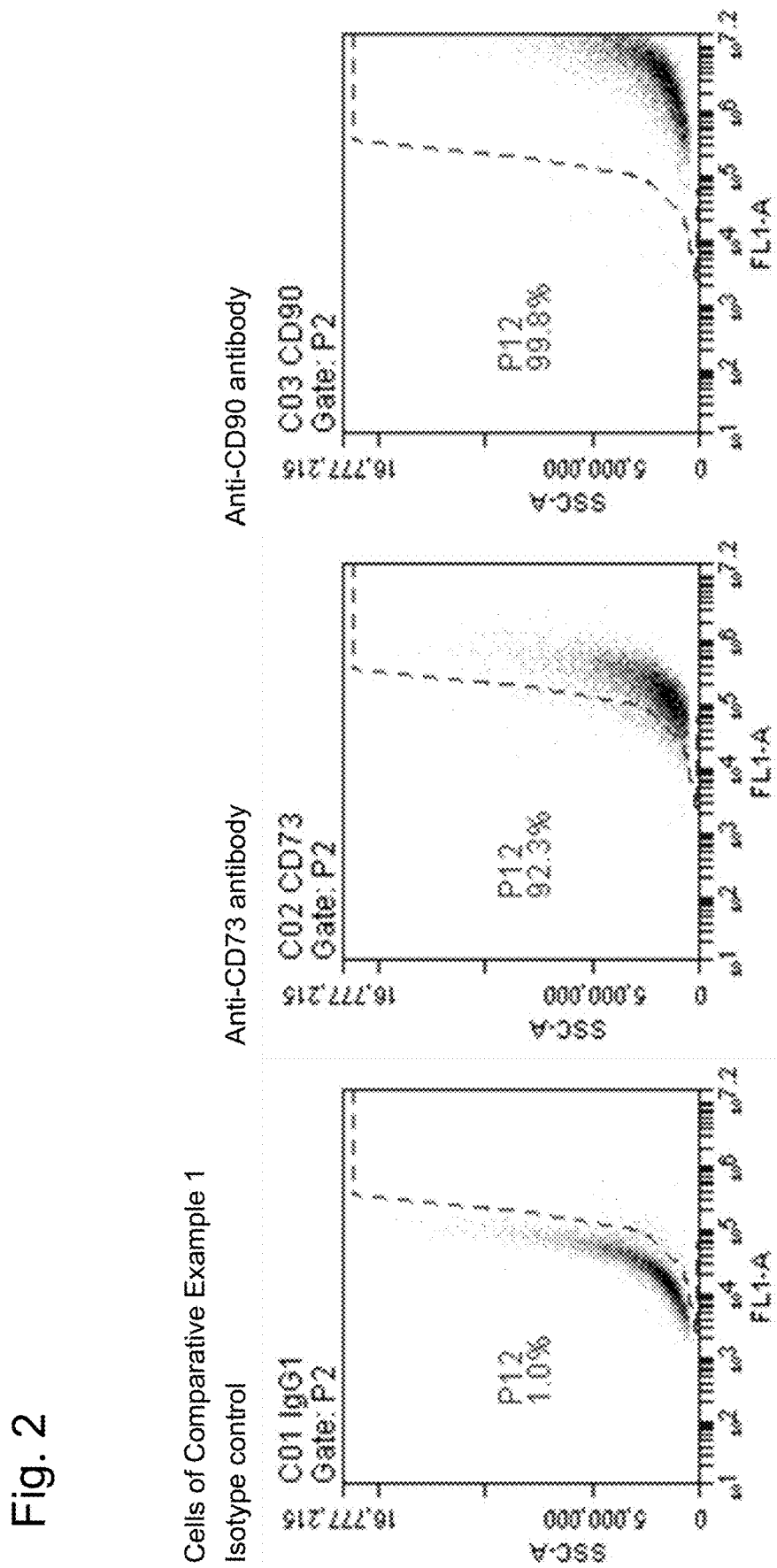
FIG. 2 shows the results of measurement of the proportion of cells positive for CD73 and CD90 using a flow cytometer as to adherent cells derived from a fetal appendage cultured in Comparative Example 1.
Figure 3:
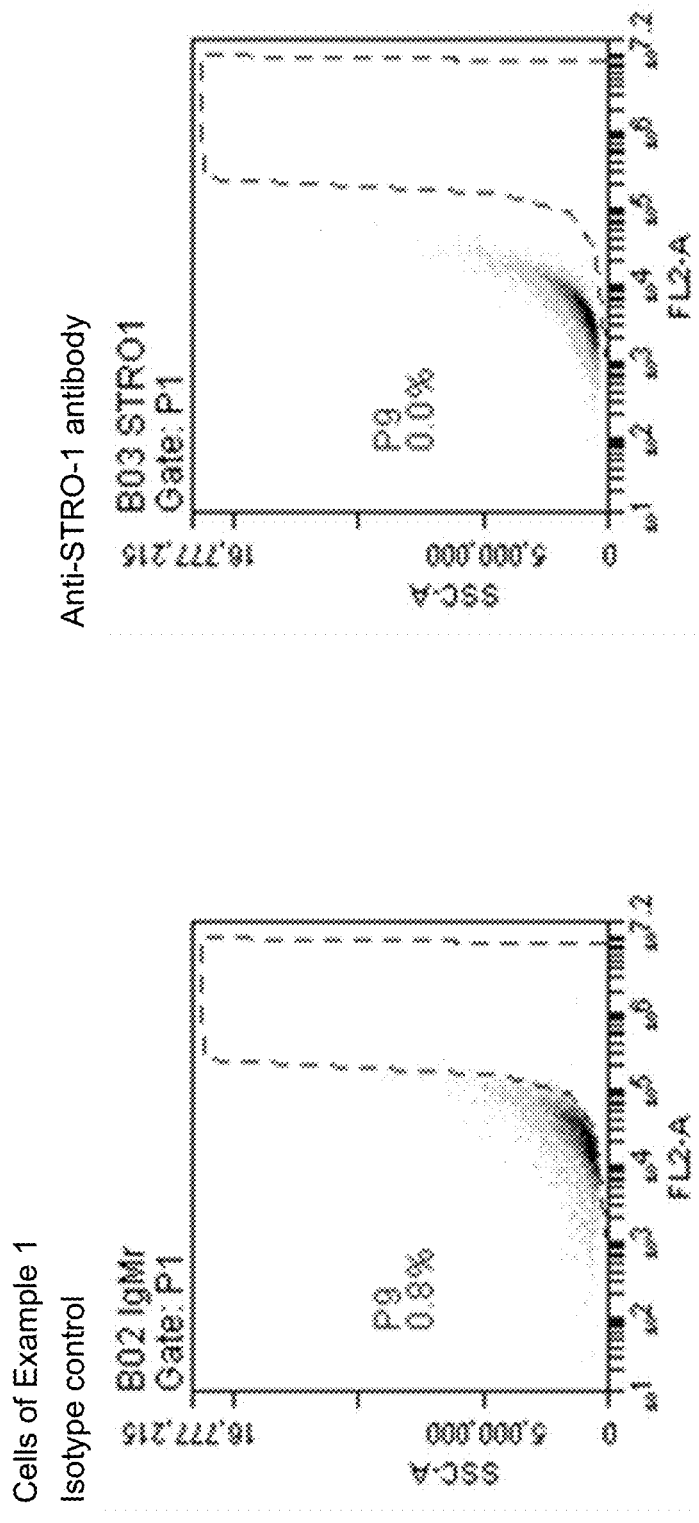
FIG. 3 shows the results of measurement of the proportion of cells positive for STRO-1 using a flow cytometer as to adherent cells derived from a fetal appendage cultured in Example 1.
Figure 4:
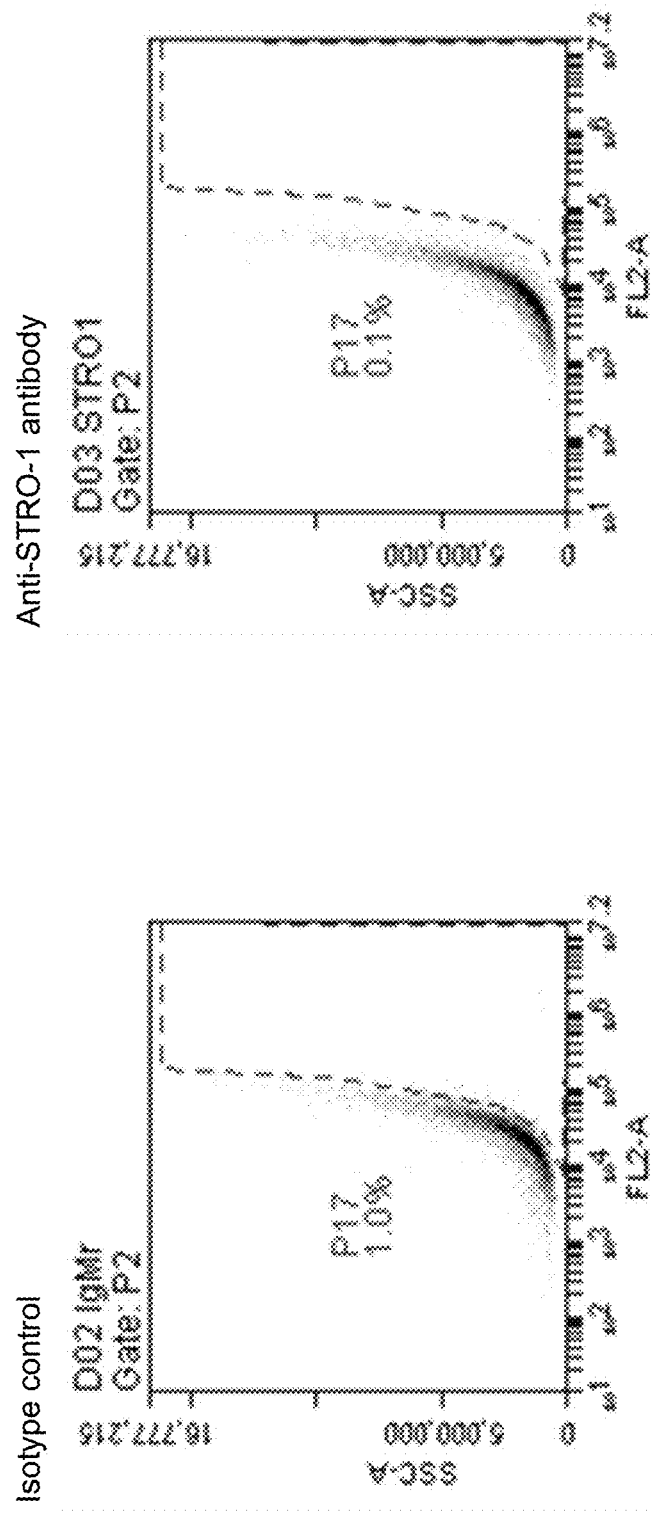
FIG. 4 shows the results of measurement of the proportion of cells positive for STRO-1 using a flow cytometer as to adherent cells derived from a fetal appendage cultured in Comparative Example 1.

Embodiments of the present invention will be specifically described below. The descriptions are intended to facilitate understanding of the principles of the present invention, and therefore, the scope of the present invention is not limited to the embodiments. Other embodiments with appropriate modifications made by a person skilled in the art are also included in the scope.

[1] Explanation of Terms

The term "fetal appendage" used herein refers to a fetal membrane, a placenta, an umbilical cord, and amniotic fluid. In addition, the term "fetal membrane" refers to a fetal sac containing fetal amniotic fluid, which comprises an amnion, a chorion, and a decidua in that order from the inside. Among them, the amnion and the chorion are originated from the fetus. The term "amnion" refers to a transparent thin membrane with few blood vessels, which is located in the most inner layer of the fetal membrane. The inner layer (also called epithelial cell layer) of the amnion is covered with a layer of epithelial cells having a secretory function and secretes amniotic fluid. The outer layer (also called extracellular matrix layer, which corresponds to the stroma) of the amnion comprises adherent cells derived from a fetal appendage.

The term "adherent cells derived from a fetal appendage" used herein refers to adherent cells derived from a fetal appendage and refers to cells that meet the definition below.

Definition of adherent cells derived from a fetal appendage
i) Derived from a fetal appendage
ii) Adherence to plastic in standard medium under culture conditions
iii) Positive for surface antigens CD105, CD73, and CD90, and negative for surface antigens CD45, CD34, CD11b, CD79alpha, CD19, and HLA-DR The term "adherent cell population derived from a fetal appendage" used herein means a cell population comprising adherent cells derived from a fetal appendage. Examples of the form thereof include, but are not particularly limited to, cell pellets, cell aggregates, cell-floated liquids, and cell suspensions.

The term "differentiation capacity" used herein refers to the ability of cells to change into other cell types with different properties. Differentiation capacity can be evaluated by cell culture using a medium for inducing differentiation described in the Examples below and microscopic observation of the cultured cells.

The phrase "the proportion of CD73- and CD90-positive adherent cells derived from a fetal appendage" used herein refers to the proportion of cells positive for the surface antigen analyzed by flow cytometry as described in Examples mentioned later. The phrase "the proportion of CD73- and CD90-positive adherent cells derived from a fetal appendage" used herein is also described as "positive rate."

The phrase "the proportion of STRO-1 negative adherent cells derived from a fetal appendage" used herein refers to the proportion of cells negative for the surface antigen analyzed by flow cytometry as described in Examples mentioned later. The phrase "the proportion of STRO-1 negative adherent cells derived from a fetal appendage" used herein is also described as "negative rate".

[2] Cell Population Comprising Adherent Cells Derived from a Fetal Appendage

The cell population comprising adherent cells derived from a fetal appendage, provided by the present invention, is characterized in that:
(a) in the cell population, the proportion of CD73- and CD90-positive adherent cells derived from a fetal appendage is 90% or more; and
(b) the cell population satisfies a relative expression level of LFA-3 gene to the expression level of SDHA gene of 1.0 or more.

According to another aspect, the cell population comprising adherent cells derived from a fetal appendage, provided by the present invention, is characterized in that:
(a) in the cell population, the proportion of CD73- and CD90-positive adherent cells derived from a fetal appendage is 90% or more; and
(b) the cell population satisfies a relative expression level of CCND2 gene to the expression level of SDHA gene of 1.5 or less.

CD73 stands for Cluster of Differentiation 73 and is a protein also known as 5-Nucleotidase (or Ecto-5'-nucleotidase) encoded by the NT5E gene.

CD90 stands for Cluster of Differentiation 90 and is a protein also known Thy-1 encoded by the THY1 gene.

LFA-3 stands for Lymphocyte Function-associated Antigen-3.

CCND2 stands for Cyclin D2.

If the cell population comprising adherent cells derived from a fetal appendage, provided by the present invention, satisfies the following conditions: the proportion of CD73- and CD90-positive adherent cells derived from a fetal appendage is 90% or more; and the relative expression level of LFA-3 gene to the expression level of SDHA gene is 1.0 or more, a cell population comprising adherent cells having low differentiation capacity derived from a fetal appendage is formed. Hence, in the present invention, the conditions can be utilized as an index for the formation of a cell population having low differentiation capacity.

According to another aspect, if the cell population comprising adherent cells derived from a fetal appendage, provided by the present invention, satisfies the following conditions: the proportion of CD73- and CD90-positive adherent cells derived from a fetal appendage is 90% or more; and the relative expression level of CCND2 gene to the expression level of SDHA gene is 1.5 or less, cell population comprising adherent cells having low differentiation capacity derived from a fetal appendage is formed. Hence, in the present invention, the conditions can be utilized as an index for the formation of a cell population having low differentiation capacity.

The proportion of CD73-positive adherent cells derived from a fetal appendage in the cell population may be 91% or more, 92% or more, 93% or more, 94% or more, 95% or more, 96% or more, 97% or more, 98% or more, 99% or more, or 100%.

The proportion of CD90-positive adherent cells derived from a fetal appendage in the cell population may be 91% or more, 92% or more, 93% or more, 94% or more, 95% or more, 96% or more, 97% or more, 98% or more, 99% or more, or 100%.

According to an aspect of the present invention, the cell population comprising adherent cells derived from a fetal appendage, provided by the present invention, may satisfy the following: the proportion of STRO-1 negative adherent cells derived from a fetal appendage is 95% or more.

In the cell population, the proportion of STRO-1 negative adherent cells derived from a fetal appendage may be 96% or more, 97% or more, 98% or more, 99% or more, or 100%.

The surface antigen markers (CD73, CD90, and STRO-1) can be detected by an arbitrary detection method known in the art. Examples of the method for detecting CD73, CD90, and STRO-1 include, but are not limited to, flow cytometry and cell staining. When cells that emit stronger fluorescence as compared with a negative control (isotype control) are detected in flow cytometry using a fluorescently labeled antibody, the cells are confirmed to be "positive" for the marker. An arbitrary antibody known in the art can be used as the fluorescently labeled antibody. Examples thereof include, but are not limited to, antibodies labeled with fluorescein isothiocyanate (FITC), phycoerythrin (PE), allophycocyanin (APC), or the like. When cells that are stained or emit fluorescence are observed under a microscope in cell staining, the cells are confirmed to be "positive" for the marker. The cell staining may be cell immunostaining using an antibody, or may be non-immune cell staining using no antibody.

Specifically, the proportion of cells positive (positive rate) for surface antigen markers (CD73, CD90, and STRO-1) can be determined using a flow cytometry dot-plot analysis by the following procedures (1) to (8):
(1) If the cells of interest are adherent cells, the adherent cells are detached from a plastic culture vessel using trypsin-EDTA (Thermo Fisher Scientific Inc.) and then recovered by centrifugation. If the cells of interest are unadherent cells, the cells are collected by centrifugation.
(2) The cells are fixed with 4% paraformaldehyde and then washed with phosphate buffer (PBS), followed by being prepared as a cell suspension in 2% BSA/PBS at $1.0 \times 10^6$ cells/mL. The cell suspension is dispensed in 100 µL aliquots.
(3) The dispensed cell suspensions are centrifuged. Then, 100 µL of 0.5% BSA/PBS is added to each of the obtained cell pellets, followed by addition of antibodies against the respective surface antigen markers or the isotype control antibodies thereof. Each reaction solution is vortexed and then allowed to stand at 4° C. for 20 minutes.

(4) After addition of 0.5% BSA/PBS, the cells are washed by centrifugation. Subsequently, the cells are suspended in 0.5% BSA/PBS and filtered through a cell strainer (35-μm nylon mesh filter) (Corning Inc./Product number: 352235).

(5) The cell suspension obtained by filter filtration is analyzed by All Event 10000 on a BD Accuri™ C6 Flow Cytometer (Becton, Dickinson and Company).

(6) The measurement results are plotted as dots on the ordinate as SSC (side scattered light) (numerical range: 0 or more and 16777215 or less) and the abscissa as fluorescence intensity of the dye labeled to the antibody (numerical range: $10^1$ or more and $10^{7.2}$ or less).

(7) In the dot plot diagram, all regions (gates) in which the cell population with higher fluorescence intensity is 1.0% or less are selected from all cells measured with the isotype control antibodies.

(8) The percentage of cells contained in the gate selected in (7) among all cells measured with the antibody against the surface antigen marker is calculated.

The percentage of cells negative (negative rate) for the surface antigen markers (CD73, CD90, and STRO-1) is calculated by the following equation:

Negative rate (%)=100−Positive rate

Examples of the timing to detect the surface antigen marker include, but are not particularly limited to, immediately after separation of cells from a biological sample, during the course of a culture step, after purification in the culture step, immediately after the Nth passage (N represents an integer of 1 or more), during the course of maintenance culture, before cryopreservation, after thawing, and before formulation as a pharmaceutical composition.

The cell population comprising adherent cells derived from a fetal appendage, provided by the present invention, satisfies a relative expression level of LFA-3 gene to the expression level of SDHA gene of 1.0 or more.

The relative expression level of LFA-3 gene to the expression level of SDHA gene may be 1.1 or more, 1.2 or more, 1.3 or more, 1.4 or more, 1.5 or more, 1.6 or more, 1.7 or more, or 1.8 or more. The upper limit of the relative expression level of LFA-3 gene to the expression level of SDHA gene is not particularly limited but may be, for example, 10.0 or less, 9.0 or less, 8.0 or less, 7.0 or less, 6.0 or less, or 5.0 or less.

According to another aspect, the cell population comprising adherent cells derived from a fetal appendage, provided by the present invention satisfies a relative expression level of CCND2 gene to the expression level of SDHA gene of 1.5 or less.

The relative expression level of CCND2 gene to the expression level of SDHA gene may be 1.4 or less, 1.3 or less, 1.2 or less, 1.1 or less, 1.0 or less, 0.9 or less, 0.8 or less, 0.7 or less, 0.6 or less, 0.5 or less, or 0.4 or less. The lower limit of the relative expression level of CCND2 gene to the expression level of SDHA gene is not particularly limited but may be, for example, 0.0 or more or 0.1 or more.

According to an aspect of the present invention, the cell population comprising adherent cells derived from a fetal appendage, provided by the present invention, may satisfy a relative expression level of HAPLN1 gene to the expression level of SDHA gene of 4.0 or more and/or a relative expression level of CCND2 gene to the expression level of SDHA gene of 1.5 or less.

The relative expression level of HAPLN1 gene to the expression level of SDHA gene may be 4.1 or more, 4.2 or more, 4.3 or more, 4.4 or more, 4.5 or more, 4.6 or more, 4.7 or more, 4.8 or more, 4.9 or more, 5.0 or more, 5.1 or more, 5.2 or more, 5.3 or more, 5.4 or more, 5.5 or more, 5.6 or more, 5.7 or more, 5.8 or more, 5.9 or more, 6.0 or more, 6.1 or more, 6.2 or more, 6.3 or more, or 6.4 or more. The upper limit of the relative expression level of HAPLN1 gene to the expression level of SDHA gene is not particularly limited and may be, for example, 15.0 or less, 14.0 or less, 13.0 or less, 12.0 or less, 11.0, or less, or 10.0 or less.

As a method of measuring the relative expression level of each gene to the expression level of SDHA gene, a measurement using a microarray can be used. Specifically, the microarray can be performed by the procedures (1) to (5) described below. Here, the following procedures (3) to (5) can be entrusted to and performed by RIKEN GENESIS Co., Ltd.

(1) From the plastic culture vessel, adherent cells are detached non-enzymatically using a cell scraper (manufactured by Corning Inc.) and the cells are then recovered by centrifugation.

(2) After stable storage of cells using a RNA stabilization reagent (RNAlater, manufactured by Thermo Fisher Scientific Inc.), total RNA is extracted and purified using a RNA extraction kit (RNeasy Plus Mini kit, manufactured by QIAGEN, Co., Ltd.).

(3) Using the purified total RNA as a template, cDNA is synthesized by reverse transcription. Then, the synthesized cDNA is further transcribed to cRNA by in vitro transcription and subjected to biotin labeling.

(4) Biotin-labeled cRNA is added to a hybridization buffer and subjected to hybridization for 16 hours on Human GeneGenome U133A 2.0 Array (manufactured by Affymetrix, Inc.). The hybridized product was washed with GeneChip Fluidics Station 450 (manufactured by Affymetrix, Inc.), and stained with phycoerythrin, followed by being scanned with GeneChip Scanner 3000 7G (manufactured by Affymetrix, Inc.). Then, the product is subjected to image analysis with AGCC (Affymetrix GeneChip Command Console Software, manufactured by Affymetrix, Inc.) and then digitized using Affymetrix Expression Console (manufactured by Affymetrix, Inc.).

(5) Numerical data files are compared and analyzed using analysis software GeneSpring GX (manufactured by Agilent Technologies, Inc.). The relative expression level of each gene to the expression level of SDHA gene in each cell is calculated.

The sequence of SDHA (Succinate dehydrogenase complex, subunit A) gene is registered as ID: 6389 in the gene database of National Center for Biotechnology Information.

The sequence of LFA-3 (Lymphocyte function-associated antigen-3) gene is registered as ID: 965 in the gene database of the National Center for Biotechnology Information.

The sequence of HAPLN1 (Hyaluronan and proteoglycan link protein 1) gene is registered as ID: 1404 in the gene database of the National Center for Biotechnology Information.

The sequence of CCND2 (Cyclin D2) gene is registered as ID: 894 in the gene database of the National Center for Biotechnology Information.

The timing to measure the gene expression level mentioned above is, but are not particularly limited to, immediately after separation of cells from a biological sample, during the course of a culture step, after purification in the culture step, immediately after the Nth passage (N represents an integer of 1 or more), during the course of maintenance culture, before cryopreservation, after thawing, and before formulation as a pharmaceutical composition.

The origin of adherent cells derived from a fetal appendage is not particularly limited as long as it is fetal appendage, but for example, adherent cells derived from fetal membrane, amnion, chorion, decidua, placenta, umbilical cord, and amniotic fluid can be used. The adherent cells derived from a fetal appendage are preferably adherent cells derived from amnion (amnion-derived adherent cells).

The adherent cells derived from a fetal appendage of the present invention can be preserved in a frozen state until immediately before use. The cell population of adherent cells derived from a fetal appendage may comprise an arbitrary component, in addition to the adherent cells derived from a fetal appendage. Examples of such a component can include, but are not limited to, salts, polysaccharides (e.g., HES and dextran), proteins (e.g., albumin), DMSO, amino acids, and medium components (e.g., components contained in RPMI1640 medium).

The cell population of the present invention may be provided as a composition in combination with a vehicle. As the vehicle, preferably a liquid vehicle (e.g., a medium or a pharmaceutical acceptable vehicle as described later) can be used.

The cell population of the present invention can include any number of adherent cells derived from a fetal appendage. The cell population of the present invention can include, but not limited to, $1 \times 10^1$, $2 \times 10^1$, $5 \times 10^1$, $1 \times 10^2$, $2 \times 10^2$, $5 \times 10^2$, $1 \times 10^3$, $2 \times 10^3$, $5 \times 10^3$, $1 \times 10^4$, $2 \times 10^4$, $5 \times 10^4$, $1 \times 10^5$, $2 \times 10^5$, $5 \times 10^5$, $1 \times 10^6$, $2 \times 10^6$, $5 \times 10^6$, $1 \times 10^7$, $2 \times 10^7$, $5 \times 10^7$, $1 \times 10^8$, $2 \times 10^8$, $5 \times 10^8$, $1 \times 10^9$, $2 \times 10^9$, $5 \times 10^9$, $1 \times 10^{10}$, $2 \times 10^{10}$, $5 \times 10^{10}$, $1 \times 10^{11}$, $2 \times 10^{11}$, $5 \times 10^{11}$, $1 \times 10^{12}$, $2 \times 10^{12}$, or $5 \times 10^{12}$ or more or less of adherent cells derived from a fetal appendage.

The differentiation capacity of the cell population can be evaluated by the following procedures (1) to (3).
(1) The cultured cell population is passaged to a 12-well plate for adherent culture (Sumitomo Bakelite, Co., Ltd./Product number: MS-80120) and cultured in aMEM(Alpha Modification of Minimum Essential Medium Eagle) containing 10% fetal serum (FBS) (inactivated) and 1×Antibiotic-Antimycotic (manufactured by Thermo Fisher Scientific Inc.) to a confluency of 60% or more and 80% or less.
(2) Using a medium for inducing differentiation into adipocytes (StemPro (registered trademark) Adipogenesis Differentiation Kit, manufactured by Thermo Fisher Scientific Inc.) or a medium for inducing differentiation into chondrocytes (StemPro (registered trademark) Chondrogenesis Differentiation Kit, manufactured by Thermo Fisher Scientific Inc.), the cultivation is carried out for 21 days in an environment at 37° C. with a $CO_2$ concentration of 3% or more and 5% or less. Medium replacement is carried out with a frequency of twice a week.
(3) The cell population cultured using a medium for inducing differentiation into adipocytes is stained with Oil Red O and observed under a microscope. The cell population cultured using a medium for inducing differentiation into chondrocytes is stained with Alcian Blue and observed under a microscope.

[3] Method for Producing Cell Population Comprising Adherent Cells Derived from a Fetal Appendage The method for producing cell population comprising adherent cells derived from a fetal appendage according to the present invention is a method comprising obtaining a cell population having the following cell characteristics (a) and (b):

(a) in the cell population, the proportion of CD73- and CD90-positive adherent cells derived from a fetal appendage is 90% or more; and
(b) the cell population satisfies a relative expression level of LFA-3 gene to the expression level of SDHA gene of 1.0 or more.

According to another aspect, the method for producing cell population comprising adherent cells derived from a fetal appendage according to the present invention is a method comprising obtaining a cell population having the following cell characteristics (a) and (b):
(a) in the cell population, the proportion of CD73- and CD90-positive adherent cells derived from a fetal appendage is 90% or more; and
(b) the cell population satisfies a relative expression level of CCND2 gene to the expression level of SDHA gene of 1.5 or less.

Specifically, the method for producing cell population comprising adherent cells derived from a fetal appendage according to the present invention is a method comprising the step of preparing the cell characteristics of the above (a) and (b). The above conditions of (a) and (b) serve as an index for the formation of a cell population comprising adherent cells having low differentiation capacity derived from a fetal appendage. The culture method of the present invention is not particularly limited as long as the index is satisfied.

The production method of the present invention may comprise a cell population obtainment step of obtaining a cell population comprising adherent cells derived from a fetal appendage by the enzyme treatment of a sample (e.g., the amnion or chorion) comprising adherent cells derived from a fetal appendage.

The amnion comprises an epithelial cell layer and an extracellular matrix layer. The latter layer comprises adherent cells derived from a fetal appendage. Like other epithelial cells, the amniotic epithelial cells are characterized in that they express epithelial cadherin (E-cadherin: CD324) and an epithelial cell adhesion factor (EpCAM: CD326) while the adherent cells derived from a fetal appendage do not express such epithelial-specific surface antigen markers. Thus, these cells can be easily distinguished by flow cytometry. The cell population obtainment step may be a step comprising the step of obtaining the amnion by cesarean section.

The cell population comprising adherent cells derived from a fetal appendage according to the present invention is preferably a cell population obtained by treating a sample comprising an epithelial cell layer and an extracellular matrix layer collected from a fetal appendage with at least collagenase.

The enzyme treatment of the sample collected from a fetal appendage (preferably a sample comprising an epithelial cell layer and a extracellular matrix layer) is preferably a treatment with an enzyme (or a combination of enzymes) that can release adherent cells derived from a fetal appendage contained in the extracellular matrix layer of the fetal appendage, and does not degrade the epithelial cell layer. Examples of such an enzyme can include, but are not particularly limited to, collagenase and/or metalloproteinase. Examples of the metalloproteinase can include, but are not particularly limited to, thermolysin and/or dispase, which is metalloproteinase that cleaves nonpolar amino acids at their N-terminal sides.

The active concentration of the collagenase is preferably 50 PU/ml or higher, more preferably 100 PU/ml or higher, further preferably 200 PU/ml or higher, further preferably 300 PU/ml or higher, and further preferably 400 PU/ml or higher. The active concentration of the collagenase is, but is not particularly limited to, for example, 1000 PU/ml or lower, 900 PU/ml or lower, 800 PU/ml or lower, 700 PU/ml or lower, 600 PU/ml or lower, or 500 PU/ml or lower. In this context, PU (protease unit) is defined as the amount of the enzyme that degrades 1 ug of FITC-collagen for 1 minute at 30° C. at pH 7.5.

The active concentration of the metalloproteinase (e.g., thermolysin and/or dispase) is preferably 50 PU/ml or higher, more preferably 100 PU/ml or higher, further preferably 200 PU/ml or higher, further preferably 300 PU/ml or higher, and further preferably 400 PU/ml or higher. Also, the active concentration of the metalloproteinase is preferably 1000 PU/ml or lower, more preferably 900 PU/ml or lower, further preferably 800 PU/ml or lower, further preferably 700 PU/ml or lower, further preferably 600 PU/ml or lower, and further preferably 500 PU/ml or lower. In this context, PU (protease unit) in an aspect of using dispase as the metalloproteinase is defined as the amount of the enzyme that releases an amino acid corresponding to 1 ug tyrosine from casein lactate for 1 minute at 30° C. at pH 7.5. In the concentration range of the enzyme described above, adherent cells derived from a fetal appendage contained in the extracellular matrix layer can be efficiently released while prevented from being contaminated with epithelial cells contained in the epithelial cell layer of the fetal appendage. The preferred combination of the concentrations of the collagenase and/or the metalloproteinase can be determined by the microscopic observation of the fetal appendage after the enzyme treatment, or the flow cytometry of the obtained cells.

It is preferred to treat the fetal appendage with collagenase and metalloproteinase in combination at the same time in one operation, from the viewpoint of efficiently recovering live cells. In this case, thermolysin and/or dispase can be used as the metalloproteinase, though the metalloproteinase is not limited thereto. The fetal appendage can be treated only once with an enzyme solution containing collagenase and metalloproteinase to conveniently obtain adherent cells derived from a fetal appendage. The treatment at the same time in one operation can reduce the risk of contamination by bacteria, viruses, and the like.

For the enzyme treatment of the fetal appendage, it is preferred to dip, in the enzyme solution, the amnion washed using a washing solution such as physiological saline or Hank's balanced salt solution, and perform the treatment with stirring using stirring means. A stirrer or a shaker can be used as such stirring means from the viewpoint of efficiently releasing adherent cells derived from a fetal appendage contained in the extracellular matrix layer of the fetal appendage, though the stirring means is not limited thereto. The stirring rate is not particularly limited and is, in the case of using a stirrer or a shaker, for example, 5 rpm or more, 10 rpm or more, 20 rpm or more, 30 rpm or more, 40 rpm or more or 50 rpm or more. Also, the stirring rate is not particularly limited and is, in the case of using a stirrer or a shaker, for example, 100 rpm or less, 90 rpm or less, 80 rpm or less, 70 rpm or less or 60 rpm or less. The enzyme treatment time is not particularly limited and is, for example, 10 minutes or longer, 20 minutes or longer, 30 minutes or longer, 40 minutes or longer, 50 minutes or longer, 60 minutes or longer, 70 minutes or longer, 80 minutes or longer or 90 minutes or longer. Also, the enzyme treatment time is not particularly limited and is, for example, 6 hours or shorter, 5 hours or shorter, 4 hours or shorter, 3 hours or shorter, 2 hours or shorter, 110 minutes or shorter, 100 minutes or shorter. The enzyme treatment temperature is not particularly limited and is, for example, 15° C. or higher, 16° C. or higher, 17° C. or higher, 18° C. or higher, 19° C. or higher, 20° C. or higher, 21° C. or higher, 22° C. or higher, 23° C. or higher, 24° C. or higher, 25° C. or higher, 26° C. or higher, 27° C. or higher, 28° C. or higher, 29° C. or higher, 30° C. or higher, 31° C. or higher, 32° C. or higher, 33° C. or higher, 34° C. or higher, 35° C. or higher or 36° C. or higher. Also, the enzyme treatment temperature is not particularly limited and is, for example, 40° C. or lower, 39° C. or lower, 38° C. or lower or 37° C. or lower.

In the production method of the present invention, if desired, the released adherent cells derived from a fetal appendage can be separated and/or recovered from the enzyme solution containing the released adherent cells derived from a fetal appendage by a known method such as a filter, centrifugation, a hollow fiber separation membrane, or a cell sorter. Preferably, the enzyme solution containing the released adherent cells derived from a fetal appendage is filtered through a filter. In an aspect of filtering the enzyme solution through a filter, only the released cells pass through the filter, whereas an undegraded epithelial cell layer remains on the filter without passing through the filter. Therefore, not only can the released adherent cells derived from a fetal appendage be easily separated and/or recovered, but the risk of contamination by bacteria, viruses, and the like can be reduced. Examples of the filter can include, but are not particularly limited to, mesh filters. The pore size (mesh size) of the mesh filter is not particularly limited and is, for example, 40 μm or larger, 50 μm or larger, 60 μm or larger, 70 μm or larger, 80 μm or larger, or 90 μm or larger. Also, the pore size of the mesh filter is not particularly limited and is, for example, 200 μm or smaller, 190 μm or smaller, 180 μm or smaller, 170 μm or smaller, 160 μm or smaller, 150 μm or smaller, 140 μm or smaller, 130 μm or smaller, 120 μm or smaller, 110 μm or smaller, or 100 μm or smaller. The filtration rate is not particularly limited. When the pore size of the mesh filter falls within the range described above, the enzyme solution containing the adherent cells derived from a fetal appendage can be filtered by free fall. This can prevent decrease in cell survival rate.

Nylon is preferably used as a material for the mesh filter. A tube containing a 40 μm, 70 μm, 95 μm or 100 μm nylon mesh filter such as a Falcon cell strainer, which is widely used for research purposes, is available. Alternatively, medical mesh cloth (nylon and polyester) used for hemodialysis and the like is available. Further, an arterial filter used for extracorporeal circulation (polyester mesh filter, pore size: 40 μm or larger and 120 μm or smaller) is also available. A mesh made of any other material, for example, a stainless-steel mesh filter, may be used.

Preferably, the adherent cells derived from a fetal appendage are allowed to pass through a filter in a free fall motion. It is also possible to force the cells to pass through a filter by suction using a pump or the like. In this case, in order to avoid damage of the cells, minimum necessary pressurization is desirable.

The adherent cells derived from the fetal append that have passed through the filter can be recovered by centrifugation after dilution of the filtrate with two times or more its volume of a medium or balanced salt buffer solution. Examples of the balanced salt buffer solution that can be used include, but are not limited to, Dulbecco's phosphate-buffered saline (DPBS), Earle's balanced salt solution (EBSS), Hank's balanced salt solution (HBSS), and phosphate-buffered saline (PBS).

The cell population obtained in the cell population obtainment step is prepared under the following conditions:
(a) in the cell population, the proportion of CD73- and CD90-positive adherent cells derived from a fetal appendage is 90% or more; and
(b) the cell population satisfies a relative expression level of LFA-3 gene to the expression level of SDHA gene of 1.0 or more.

According to another aspect, the cell population obtained in the cell population obtainment step is prepared under the following conditions:
(a) in the cell population, the proportion of CD73- and CD90-positive adherent cells derived from a fetal appendage is 90% or more; and
(b) the cell population satisfies a relative expression level of CCND2 gene to the expression level of SDHA gene of 1.5 or less.

The conditions are useful as an index for obtaining a cell population comprising adherent cells having low differentiation capacity derived from a fetal appendage. The preparation method is not particularly limited as long as the index is satisfied. Examples of such a method can include for example, obtaining a cell population satisfying the above (a) with a cell sorter, and then selecting a cell population satisfying the above (b) from the obtained cell population; and selecting a cell population satisfying the above (b), and then obtaining a cell population satisfying the above (a) with a cell sorter from the obtained cell population. In addition, examples of preparation methods that satisfy the index include culturing a cell population under the conditions satisfying the above (a) and (b).

Examples of the culture method that satisfies the index can include the step of repeating a plurality of times the inoculation of the cell population onto an uncoated plastic culture vessel at a density of 400 to 5,000 cells/cm$^2$, followed by culture. The density of the cell population for inoculation is more preferably 500 cells/cm$^2$ or more, further preferably 600 cells/cm$^2$ or more, further preferably 700 cells/cm$^2$ or more, further preferably 800 cells/cm$^2$ or more, further preferably 900 cells/cm$^2$ or more, further preferably 1000 cells/cm$^2$ or more, further preferably 1100 cells/cm$^2$ or more, further preferably 1200 cells/cm$^2$ or more, further preferably 1300 cells/cm$^2$ or more, further preferably 1400 cells/cm$^2$ or more, further preferably 1500 cells/cm$^2$ or more, further preferably 1600 cells/cm$^2$ or more, further preferably 1700 cells/cm$^2$ or more, further preferably 1800 cells/cm$^2$ or more, further preferably 1900 cells/cm$^2$ or more, and further preferably 2000 cells/cm$^2$ or more. The density of the cell population for inoculation is more preferably 4800 cells/cm$^2$ or less, further preferably 4600 cells/cm$^2$ or less, further preferably 4400 cells/cm$^2$ or less, further preferably 4200 cells/cm$^2$ or less, further preferably 4000 cells/cm$^2$ or less, further preferably 3800 cells/cm$^2$ or less, further preferably 3600 cells/cm$^2$ or less, further preferably 3400 cells/cm$^2$ or less, further preferably 3200 cells/cm$^2$ or less, further preferably 3000 cells/cm$^2$ or less, further preferably 2800 cells/cm$^2$ or less, further preferably 2600 cells/cm$^2$ or less, further preferably 2400 cells/cm$^2$ or less, and further preferably 2200 cells/cm$^2$ or less.

Examples of the other culture methods that satisfy the index can include the step of repeating a plurality of times the inoculation of the cell population onto a plastic culture vessel coated with a coating agent at a density of 400 to 5,000 cells/cm$^2$, followed by culture. Preferred density conditions for the inoculation of the cell population are similar to those described above.

Examples of the coating agent can include, but are not limited to, extracellular matrix, fibronectin, vitronectin, osteopontin, laminin, entactin, collagen I, collagen II, collagen III, collagen IV, collagen V, collagen VI, gelatin, poly-L-ornithine, poly-D-lysine, and Matrigel® matrix.

Examples of the other culture methods that satisfy the index is culturing with addition of basic fibroblast growth factor (bFGF) to the basal medium for use in the culture. The concentration of the basic fibroblast growth factor is preferably 2 ng/mL or more, further preferably 4 ng/mL or more, further preferably 6 ng/mL or more, further preferably 8 ng/mL or more, or further preferably 10 ng/mL or more. The concentration of the basic fibroblast growth factor is preferably 20 ng/mL or less, further preferably 18 ng/mL or less, 16 ng/mL or less, further preferably 14 ng/mL or less, or further preferably 12 ng/mL or less. The timing of adding the basic fibroblast growth factor is not particularly limited and is, for example, at the beginning of the culture step, during the course of a culture step, after purification in the culture step, immediately after the Nth passage (N represents an integer of 1 or more), during the course of maintenance culture, before cryopreservation, or after thawing.

Examples of the culture period of one culture process can include 4 to 10 days and can more specifically include 4 days, 5 days, 6 days, 7 days, 8 days, 9 days and 10 days.

The medium for use in the culture can be prepared by utilizing an arbitrary liquid medium for animal cell culture as a basal medium and, if necessary, appropriately adding thereto other components (serum, a serum replacement reagent, a growth factor, etc.).

Examples of the basal medium that can be used include, but are not particularly limited to, media such as BME medium, BGJb medium, CMRL1066 medium, Glasgow MEM medium, improved MEM zinc option medium, IMDM medium (Iscove's modified Dulbecco's medium), Medium 199 medium, Eagle MEM medium, αMEM (alpha modification of minimum essential medium eagle) medium, DMEM medium (Dulbecco's modified Eagle's medium), Ham's F10 medium, Hams' F12 medium, RPMI 1640 medium, Fischer's medium, and mixed media thereof (e.g., DMEM/F12 medium (Dulbecco's modified Eagle's medium/nutrient mixture F-12 Ham)).

Alternatively, the medium for use in the culture may be a commercially available serum-free medium. Examples thereof include, but are not particularly limited to, STK1 and STK2 (DS Pharma Biomedical Co., Ltd.).

Examples of other components to be added to the basal medium include albumin, serum, serum replacement reagents and growth factors. In an aspect of adding albumin to the basal medium, the concentration of albumin is preferably higher than 0.05% and 5% or lower. Also, in an aspect of adding serum to the basal medium, the concentration of serum is preferably 5% or higher. In an aspect of adding a growth factor, the medium may be prepared by adding a reagent (heparin, etc.) for stabilizing the growth factor in the medium, to the growth factor, and further adding the mixture to the basal medium, or may be prepared by stabilizing the growth factor in advance with a gel, a polysaccharide, or the like, and then adding the stabilized growth factor to the basal medium.

The culture of adherent cells derived from a fetal appendage can be performed by, for example, the following process: first, a cell suspension is centrifuged. The supernatant is removed, and the obtained cell pellet is suspended in a medium. Next, the cells are inoculated to a plastic culture vessel and cultured using a medium in an environment of a $CO_2$ concentration of 3% or higher and 5% or lower at 37°

C. until 95% or less confluence. Examples of the medium can include, but are not limited to, aMEM, M199, and media based thereon. The cells obtained by the culture as described above are cells cultured once.

The cells cultured once can be further passaged and cultured, for example, as follows: first, the cells cultured once are dissociated from the plastic culture vessel by treatment with ethylenediaminetetraacetic acid (EDTA) followed by treatment with trypsin. Next, the obtained cell suspension is centrifuged. The supernatant is removed, and the obtained cell pellet is suspended in a medium. Finally, the cells are inoculated to a plastic culture vessel and cultured using a medium in an environment of a $CO_2$ concentration of 3% or higher and 5% or lower at 37° C. until 95% or less confluence. Examples of the medium can include, but are not limited to, aMEM, M199, and media based thereon. The cells obtained by the passage and the culture as described above are cells passaged once. Cells passaged N times can be obtained by similar passage and culture (N represents an integer of 1 or more). The lower limit of passage number N is, for example, 1 or more, preferably 2 or more, more preferably 3 or more, further preferably 4 or more, further preferably 5 or more, further preferably 6 or more, further preferably 7 or more, further preferably 8 or more, further preferably 9 or more, further preferably 10 or more, further preferably 11 or more, further preferably 12 or more, further preferably 13 or more, further preferably 14 or more, further preferably 15 or more, further preferably 16 or more, further preferably 17 or more, further preferably 18 or more, further preferably 19 or more, further preferably 20 or more, and further preferably 25 or more, from the viewpoint of producing the cells at a large scale. Also, the upper limit of passage number N is, for example, preferably 50 or less, 45 or less, 40 or less, 35 or less, or 30 or less, from the viewpoint of suppressing cell senescence.

According to the production method of the present invention, cell population comprising adherent cells having low differentiation capacity derived from a fetal appendage can be obtained. This enables production of a safer cell preparation (pharmaceutical composition). The lower limit of the obtained cell count per batch of culture (cell count obtained per unit surface area and per unit number of culture days) differs depending on an inoculated cell count, an inoculation density, etc. and is, for example, $1.0\times10^5$ (cells/cm$^2$/day) or more, $2.0\times10^5$ (cells/cm$^2$/day) or more, $3.0\times10^5$ (cells/cm$^2$/day) or more, $4.0\times10^5$ (cells/cm$^2$/day) or more, $5.0\times10^5$ (cells/cm$^2$/day) or more, $6.0\times10^5$ (cells/cm$^2$/day) or more, $7.0\times10^5$ (cells/cm$^2$/day) or more, $8.0\times10^5$ (cells/cm$^2$/day) or more, $9.0\times10^5$ (cells/cm$^2$/day) or more or $10.0\times10^5$ (cells/cm$^2$/day) or more. Also, the upper limit of the obtained cell count per batch of culture is not particularly limited and is, for example, $10.0\times10^8$ (cells/cm$^2$/day) or less, $9.0\times10^8$ (cells/cm$^2$/day) or less, $8.0\times10^8$ (cells/cm$^2$/day) or less, $7.0\times10^8$ (cells/cm$^2$/day) or less, $6.0\times10^8$ (cells/cm$^2$/day) or less, $5.0\times10^8$ (cells/cm$^2$/day) or less, $4.0\times10^8$ (cells/cm$^2$/day) or less, $3.0\times10^8$ (cells/cm$^2$/day) or less, $2.0\times10^8$ (cells/cm$^2$/day) or less or $1.0\times10^8$ (cells/cm$^2$/day) or less.

According to the production method of the present invention, cell population comprising adherent cells having low differentiation capacity derived from a fetal appendage can be obtained. The adherent cells derived from a fetal appendage obtained by the production method of the present invention are thereby culturable preferably up to 40 days or later, and more preferably up to 45 days or later, up to 50 days or later, up to 55 days or later, up to 60 days or later, up to 65 days or later, up to 70 days or later, up to 75 days or later, up to 80 days or later, up to 85 days or later, up to 90 days or later, up to 95 days or later, up to 100 days or later, up to 105 days or later, or up to 110 days or later, after the start of in vitro culture.

The adherent cells derived from a fetal appendage obtained by the production method of the present invention are also culturable up to a population doubling level of preferably 10 or more, and more preferably 15 or more, 20 or more, 25 or more, 30 or more, 35 or more, 40 or more, 45 or more, or 50 or more, after the start of in vitro culture.

The production method of the present invention may comprise an identification step of identifying a cell population comprising adherent cells having low differentiation capacity derived from a fetal appendage by utilizing, as an index, the following conditions:
(a) in the cell population, the proportion of CD73- and CD90-positive adherent cells derived from a fetal appendage is 90% or more; and
(b) the cell population satisfies a relative expression level of LFA-3 gene to the expression level of SDHA gene of 1.0 or more.

In another aspect, the production method of the present invention may comprise an identification step of identifying a cell population comprising adherent cells having low differentiation capacity derived from a fetal appendage by utilizing, as an index, the following conditions:
(a) in the cell population, the proportion of CD73- and CD90-positive adherent cells derived from a fetal appendage is 90% or more; and
(b) the cell population satisfies a relative expression level of CCND2 gene to the expression level of SDHA gene of 1.5 or less.

Means for identifying the cell population comprising adherent cells derived from a fetal appendage are preferably flow cytometry and a microarray.

The proportion of CD73- and CD90-positive adherent cells derived from a fetal appendage (positive rate) in the cell population can be measured according to the procedure described in paragraph 0033 using a flow cytometry dot-plot analysis.

The relative expression level of LFA-3 gene and CCND2 gene to the expression level of SDHA gene can be measured according to the procedure described in paragraph 0042 using a microarray.

The timing to perform the above identification is, but are not particularly limited to, immediately after separation of cells from a biological sample, during the course of a culture step, after purification in the culture step, immediately after the Nth passage (N represents an integer of 1 or more), during the course of maintenance culture, before cryopreservation, after thawing, and before formulation as a pharmaceutical composition.

The production method of the present invention can comprise the step of identifying cell population comprising adherent cells derived from a fetal appendage by utilizing, as an index, the above (a) and (b), followed by selective separation of the identified cell population. Means for selectively separating the identified cell population is not particularly limited and is, for example, separation of the cell populations by a cell sorter and purification of the cell population by culture.

The production method of the present invention can also comprise the step of cryopreserving the cell population comprising adherent cells derived from a fetal appendage. In an aspect comprising the step of cryopreserving the cell population, the cell population may be thawed, and then, if necessary, separated, recovered and/or cultured. Alternatively, the cell population may be thawed and then directly used.

Examples of the means for cryopreserving cell population comprising adherent cells derived from a fetal appendage include, but are not particularly limited to, programmable freezers, deep freezers, and dipping in liquid nitrogen. When a programmable freezer is used, the temperature for freezing is preferably −30° C. or lower, −40° C. or lower, −50° C. or lower, −60° C. or lower, −70° C. or lower, −80° C. or lower, −90° C. or lower, −100° C. or lower, −110° C. or lower, −120° C. or lower, −130° C. or lower, −140° C. or lower, −150° C. or lower, −160° C. or lower, −170° C. or lower, −180° C. or lower, −190° C. or lower, or −196° C. (liquid nitrogen temperature) or lower. When a programmable freezer is used, the freezing rate for freezing is, for example, preferably −1° C./min, −2° C./min, −3° C./min, −4° C./min, −5° C./min, −6° C./min, −7° C./min, −8° C./min, −9° C./min, −10° C./min, −11° C./min, −12° C./min, −13° C./min, −14° C./min or −15° C./min. In the case of using a programmable freezer as such freezing means, the temperature can be lowered to a temperature between −50° C. or higher and −30° C. or lower (e.g., −40° C.) at a freezing rate of, for example, −2° C./min or more and −1° C./min or less, and further lowered to a temperature of −100° C. or higher and −80° C. or lower (e.g., −90° C.) at a freezing rate of −11° C./min or more and −9° C./min or less (e.g., −10° C./min). In the case of using dipping in liquid nitrogen as such freezing means, the temperature can be rapidly lowered to a temperature of −196° C. to freeze, and then cryopreservation can be performed in liquid nitrogen (gas phase).

For freezing by the freezing means, the cell population may be frozen in a state contained in an arbitrary preservation container. Examples of such a preservation container include, but are not limited to, cryotubes, cryovials, bags for freezing, and infusion bags.

For freezing by the freezing means, the cell population may be frozen in any cryopreservation solution. Examples of such a cryopreservation solution include, but are not limited to, commercially available cryopreservation solutions, such as CryoNovo (Akron Biotechnology, LLC.) and CryoStor (HemaCare Inc.).

The cryopreservation solution can contain polysaccharides at a predetermined concentration. The preferred concentration of polysaccharides is, for example, 1% by mass or higher, 2% by mass or higher, 3% by mass or higher, 4% by mass or higher, 5% by mass or higher, 6% by mass or higher, 7% by mass or higher, 8% by mass or higher, 9% by mass or higher, 10% by mass or higher, 11% by mass or higher, or 12% by mass or higher. Alternatively, the preferred concentration of polysaccharides is, for example, 40% by mass or lower, 35% by mass or lower, 30% by mass or lower, 25% by mass or lower, 20% by mass or lower, 19% by mass or lower, 18% by mass or lower, 17% by mass or lower, 16% by mass or lower, 15% by mass or lower, 14% by mass or lower, or 13% by mass or lower. Examples of polysaccharides can include, but not limited to, hydroxylethyl starch (HES) and dextran (e.g., Dextran 40).

The cryopreservation solution can contain dimethylsulfoxide (DMSO) at a predetermined concentration. The preferable concentration of DMSO is, for example, 1% by mass or higher, 2% by mass or higher, 3% by mass or higher, 4% by mass or higher, 5% by mass or higher, 6% by mass or higher, 7% by mass or higher, 8% by mass or higher, or 9% by mass or higher. Alternatively, the preferable concentration of DMSO is, for example, 20% by mass or lower, 19% by mass or lower, 18% by mass or lower, 17% by mass or lower, 16% by mass or lower, 15% by mass or lower, 14% by mass or lower, 13% by mass or lower, 12% by mass or lower, 11% by mass or lower, or 10% by mass or lower.

The cryopreservation solution may contain albumin at a predetermined concentration larger than 0% by mass. The preferable concentration of the albumin is, for example, preferably 0.5% by mass or higher, 1% by mass or higher, 2% by mass or higher, 3% by mass or higher, 4% by mass or higher, 5% by mass or higher, 6% by mass or higher, 7% by mass or higher or 8% by mass or higher. Also, the preferable concentration of the albumin is, for example, preferably 40% by mass or lower, 35% by mass or lower, 30% by mass or lower, 25 by mass or lower, 20% by mass or lower, 15% by mass or lower, 10% by mass or lower or 9% by mass or lower. Examples of the albumin can include, but are not limited to, bovine serum albumin, mouse albumin, and human albumin.

[4] Pharmaceutical Composition

The cell population comprising adherent cells derived from a fetal appendage according to the present invention can be used as a pharmaceutical composition. Specifically, the present invention provides a pharmaceutical composition comprising the cell population according to the present invention and a pharmaceutically acceptable vehicle.

The pharmaceutical composition of the present invention is preferably a liquid preparation, more preferably an injectable liquid preparation.

The pharmaceutical composition of the present invention can be used as a cell therapy agent, for example, a therapeutic agent for intractable diseases.

The pharmaceutical composition of the present invention can be used as a therapeutic agent for a disease selected from immunological diseases, ischemic diseases, lower-limb ischemia, cerebrovascular ischemia, kidney ischemia, lung ischemia, neurological diseases, graft-versus-host disease, inflammatory bowel disease, Crohn's disease, ulcerous colitis, radiation enteritis, systemic lupus erythematosus, lupus erythematosus, collagen disease, stroke, cerebral infarction, intracerebral hematoma, cerebrovascular paralysis, liver cirrhosis, atopic dermatitis, multiple sclerosis, psoriasis, epidermolysis bullosa, diabetes mellitus, mycosis fungoides, scleroderma, inflammatory arthritis, rheumatoid arthritis, eye diseases, angiogenesis-related diseases, ischemic heart disease, coronary heart disease, myocardial infarction, angina pectoris, cardiac failure, cardiomyopathy, valvular disease, wound, epithelial damage, fibrosis, lung diseases, and cancers, and the like. The pharmaceutical composition of the present invention can be administered in a measurably effective amount to a treatment site to thereby treat the disease.

The present invention provides the cell population comprising adherent cells derived from a fetal appendage according to the present invention for use in a pharmaceutical composition.

The present invention provides the cell population comprising adherent cells derived from a fetal appendage according to the present invention for use in a cell therapy agent.

The present invention provides the cell population comprising adherent cells derived from a fetal appendage according to the present invention for use in the treatment of a disease selected from immunological diseases, ischemic diseases, lower-limb ischemia, cerebrovascular ischemia, kidney ischemia, lung ischemia, neurological diseases, graft-versus-host disease, inflammatory bowel disease, Crohn's disease, ulcerous colitis, radiation enteritis, systemic lupus erythematosus, lupus erythematosus, collagen disease, stroke, cerebral infarction, intracerebral hematoma, cerebrovascular paralysis, liver cirrhosis, atopic dermatitis, multiple sclerosis, psoriasis, epidermolysis bullosa, diabetes mellitus, mycosis fungoides, scleroderma, inflammatory arthritis, rheumatoid arthritis, eye diseases, angiogenesis-related diseases, ischemic heart disease, coronary heart disease, myocardial infarction, angina pectoris, cardiac failure, cardiomyopathy, valvular disease, wound, epithelial damage, fibrosis, lung diseases, and cancers.

The present invention provides the cell population comprising adherent cells derived from a fetal appendage according to the present invention for use in the regeneration of cardiac muscle, the production of cardiac muscle cells, angiogenesis, the repair of a blood vessel, or the suppression of immune response by administration to a patient or a subject.

The present invention provides a method for transplanting cells to a patient or a subject, and a method for treating a disease in a patient or a subject, comprising the step of administering a therapeutically effective amount of the cell population comprising adherent cells derived from a fetal appendage according to the present invention to the patient or the subject.

The present invention provides use of the cell population comprising adherent cells derived from a fetal appendage according to the present invention for the production of a pharmaceutical composition.

The present invention provides use of the cell population comprising adherent cells derived from a fetal appendage according to the present invention for the production of a cell therapy agent.

The present invention provides use of the cell population comprising adherent cells derived from a fetal appendage according to the present invention for the production of a therapeutic agent for a disease selected from immunological diseases, ischemic diseases, lower-limb ischemia, cerebrovascular ischemia, kidney ischemia, lung ischemia, neurological diseases, graft-versus-host disease, inflammatory bowel disease, Crohn's disease, ulcerous colitis, radiation enteritis, systemic lupus erythematosus, lupus erythematosus, collagen disease, stroke, cerebral infarction, intracerebral hematoma, cerebrovascular paralysis, liver cirrhosis, atopic dermatitis, multiple sclerosis, psoriasis, epidermolysis bullosa, diabetes mellitus, mycosis fungoides, scleroderma, inflammatory arthritis, rheumatoid arthritis, eye diseases, angiogenesis-related diseases, ischemic heart disease, coronary heart disease, myocardial infarction, angina pectoris, cardiac failure, cardiomyopathy, valvular disease, wound, epithelial damage, fibrosis, lung diseases, and cancers.

The dose of the pharmaceutical composition of the present invention is the amount of cells that allows a patient or a subject to whom the pharmaceutical composition has been administered to obtain therapeutic effects on the disease, compared with a patient or a subject to whom the pharmaceutical composition has not been administered. A specific dose can be appropriately determined depending on the form of administration, an administration method, intended use, and patient's or subject's age, body weight, and symptoms, and the like. A single dose of the adherent cells derived from a fetal appendage to a human is not particularly limited and is, for example, $10^4$ cells/kg body weight or more, $10^5$ cells/kg body weight or more or $10^6$ cells/kg body weight or more. Also, a single dose of the adherent cells derived from a fetal appendage to a human is not particularly limited and is, for example, $10^9$ cells/kg body weight or less, $10^8$ cells/kg body weight or less or $10^7$ cells/kg body weight or less.

Examples of the method for administering the pharmaceutical composition of the present invention include, but are not particularly limited to, subcutaneous injection, intralymph nodal injection, intravenous injection, intraarterial injection, intraperitoneal injection, intrathoracic injection, direct localized injection, and direct localized transplantation. Examples of known methods for administering the pharmaceutical composition include intravenous injection, intravenous drip injection, local direct injection, local direct transplantation, and the like as described in JP Patent Publication (Kokai) No. 2015-61520 A (2015) and Onken J E, et al. American College of Gastroenterology Conference 2006 Las Vegas, Nev., Abstract 121., Garcia-Olmo D, et al. Dis Colon Rectum 2005; 48: 1416-23. The pharmaceutical composition according to the present invention can also be administered by various methods described in these documents.

The pharmaceutical composition of the present invention may be used as an injectable preparation, an implantable preparation having a cell aggregate or sheet-like structure, or a gel preparation mixed with an arbitrary gel, for the purpose of treating other diseases.

The patient or the subject of the present invention is typically a human and may be other animals. Examples of other animals include, but are not limited to, mammal such as dogs, cats, cows, horses, pigs, goats, sheep, monkeys (cynomolgus monkeys, rhesus monkeys, common marmosets, and Japanese monkeys), ferrets, rabbits, rodents (mice, rats, gerbils, guinea pigs, and hamsters), and birds such as chickens and quails.

The pharmaceutical composition of the present invention can be preserved in a frozen state until immediately before use. When administering the pharmaceutical composition of the present invention to the patient or the subject, it can be rapidly thawed at 37° C. and used.

The pharmaceutical composition of the present invention may comprise an arbitrary component for use in the treatment of humans. Examples of such a component can include, but are not limited to, salts, polysaccharides (e.g., HES and dextran), proteins (e.g., albumin), DMSO, amino acids, and medium components (e.g., components contained in RPMI1640 medium).

The pharmaceutical composition of the present invention may be a cell population comprising adherent cells derived from a fetal appendage diluted with an infusion preparation for use as a pharmaceutically acceptable vehicle. The term "infusion preparation (pharmaceutically acceptable vehicle)" used herein is not particularly limited as long as it is a solution for use in the treatment of humans. Examples thereof include physiological saline, 5% glucose solution, Ringer's solution, lactated Ringer's solution, acetated Ringer's solution, starter solution (Solution I), rehydration solution (Solution II), maintenance infusion (Solution III), and postoperative recovery solution (Solution IV).

The pharmaceutical composition of the present invention may contain various additives for increasing preservation stability, sterility, isotonicity, absorbability and/or viscosity. Examples of the additives may include emulsifiers, dispersants, buffers, preservatives, wetting agents, antimicrobial agents, antioxidants, chelating agents, thickeners, gelling agents, pH adjusters, and the like. Examples of the thickener include, but are not limited to, HES, dextran, methylcellulose, xanthan gum, carboxymethylcellulose, hydroxypropyl cellulose, and the like. The concentration of the thickener can be optionally set according to the selected thickener, within the range of concentration that is safe when administered to the patient or the subject and achieves the desired viscosity.

The pH of the pharmaceutical composition of the present invention can be adjusted to almost neutral pH, for example, pH 6.5 or more or pH 7.0 or more, and pH 8.5 or lower or pH 8.0 or lower, but not limited thereto.

The present invention will be specifically described with reference to the Examples below; however, the present invention is not limited to the Examples.

EXAMPLES

Comparative Example 1

(Step 1: Collection of Amnion)

A fetal membrane and a placenta were aseptically collected as the fetal appendage from a pregnant woman (doner) who was an elective cesarean section case after the obtaining of informed consent. The obtained fetal membrane and placenta were contained in a sterile tray containing physiological saline. An amnion was manually separated from the stump of the fetal membrane. The amnion was washed with a Hank's balanced salt solution (free of Ca and Mg) to remove attached blood and clots.

(Step 2: Enzyme Treatment of Amnion and Recovery of Adherent Cells Derived from a Fetal Appendage)

The amnion comprising an epithelial cell layer and an extracellular matrix layer was dipped in a Hank's balanced salt solution (containing Ca and Mg) containing 300 PU/mL collagenase and 200 PU/mL dispase I. The amnion was enzyme-treated by shaking and stirring under conditions of 37° C., 90 minutes, and 50 rpm. The solution thus enzyme-treated was filtered through a nylon mesh having openings of 95 mm for the removal of undigested products of the amnion to recover a cell suspension containing adherent cells derived from a fetal appendage. The obtained cell suspension was analyzed for the proportion of cells positive for the expression of CD90 using a flow cytometer. As a result, it was confirmed that adherent cells derived from a fetal appendage were able to be separated with high purity from the amnion.

The surface antigen analysis employed BD Accuri™ C6 Flow Cytometer from Becton, Dickinson and Company, and the measurement conditions involved analyzed cell count: 10,000 cells and flow rate setting: Slow (14 µL/min). FITC Mouse Anti-Human CD90 (Becton, Dickinson and Company/model number: 561969) was used as the antibody against the CD90 antigen, and, as an isotype control antibody, FITC Mouse IgG1, κ Isotype Control (Becton, Dickinson and Company/model number: 349041) was used.

(Step 3: Cryopreservation of Adherent Cells Derived from a Fetal Appendage)

The cell population obtained in the above section "Step 2: Enzyme treatment of amnion and recovery of adherent cells derived from a fetal appendage" is suspended in BAM-BANKER (LYMPHOTEC Inc.) so as to be $1.0 \times 10^7$ cells/mL and then aliquoted into cryotubes. The cryotubes were placed in BICELL (freezing container) (NIHON FREEZER CO., LTD.) and stored at −80° C. for 12 hours, followed by being cryopreserved at liquid nitrogen temperature.

(Step 4: Culture of Adherent Cells Derived from a Fetal Appendage)

The cell population obtained in the above section "Step 3: Cryopreservation of adherent cells derived from a fetal appendage" was inoculated to an uncoated plastic culture vessel and adherently cultured until subconfluent in aMEM (alpha modification of minimum essential medium Eagle) containing 10% fetal bovine serum (FBS) (inactivated) and lxAntibiotic-Antimycotic(manufactured by Thermo Fisher Scientific Inc.). Then, the cells were dissociated using TrypLE Select (1×) (manufactured by Thermo Fisher Scientific Inc.). A ¼ amount of the cells was inoculated to an uncoated plastic culture vessel at the same scale as that of the preceding culture and thereby subcultured. Medium replacement was carried out with a frequency of twice a week. Thus, the subculture was continued.

Example 1

(Step 1: Collection of Amnion)

The amnion was obtained in the same manner as in Step 1 of Comparative Example 1 except that the fetal membrane and the placenta, which are the fetal appendages, were aseptically collected from a donor different from the donor in Comparative Example 1.

(Step 2: Enzyme Treatment of Amnion and Recovery of Adherent Cells Derived from a Fetal Appendage)

A cell suspension containing adherent cells derived from a fetal appendage was recovered by the same procedures as in Step 2 of Comparative Example 1. The obtained cell suspension was analyzed using a flow cytometer for the proportion of cells positive for the expression of CD90 by the same procedures as in Comparative Example 1. As a result, it was confirmed that adherent cells derived from a fetal appendage were able to be separated with high purity from the amnion.

(Step 3: Cryopreservation of Adherent Cells Derived from a Fetal Appendage)

The cell population obtained in the above section "Step 2: Enzyme treatment of amnion and recovery of adherent cells derived from a fetal appendage" was cryopreserved by the same procedures as in Step 3 of Comparative Example 1.

(Step 4: Culture of Adherent Cells Derived from a Fetal Appendage)

The cell population obtained in the above section "Step 3: Cryopreservation of adherent cells derived from a fetal appendage" was adherent cultured until subconfluent by the same procedures as in Step 4 of Comparative Example 1. Subculture was carried by the same procedures as in Step 4 of Comparative Example 1.

<Analysis of Surface Antigen Expression>

For the cell populations of the 6th passage cultured in Comparative Example 1 and Example 1, the proportions of cells positive for CD73, CD90, and STRO-1 were respectively measured using a flow cytometer. Alternatively, the proportion of cells negative for STRO-1 was measured using the equation described in paragraph 0034.

In this assay, FITC Mouse Anti-Human CD73 (Becton, Dickinson and Company/model number: 561254) was used as an antibody corresponding to CD73 antigen, FITC Mouse Anti-Human CD90 (Becton, Dickinson and Company/model number: 561969) was used as an antibody corresponding to CD90 antigen, FITC Mouse IgG1, κ Isotype Control (Becton, Dickinson and Company/model number: 349041) was used as their isotype control antibodies. PE Mouse Anti-STRO-1 (Abcam Co., Ltd./model number: ab190282) was used as an antibody corresponding to STRO-1 antigen, and Mouse IgM, lambda monoclonal (PE)-Isotype Control (Abcam Co., Ltd./model number: ab154448) was used as isotype control antibody.

The analysis results are shown in FIGS. 1 to 4 and Table 1.

TABLE 1

Surface antigen analysis of each cell population by flow cytometry (dot-plot analysis)

|  | Cell population of Example 1 | Cell population of Comparative Example 1 |
|---|---|---|
| (positive rate, %) | | |
| CD73 | 99.9 | 92.3 |
| CD90 | 99.9 | 99.8 |
| STRO-1 | 0.0 | 0.1 |
| (negative rate, %) | | |
| STRO-1 | 100.0 | 99.9 |

As shown in Table 1, in the cell populations of Example 1 and Comparative Example 1, the proportions of CD73-positive adherent cells derived from a fetal appendage were 90% or more (cell population of Example 1: 99.9% and cell population of Comparative Example 1: 92.3%), the proportions of CD90-positive adherent cells derived from a fetal appendage were 90% or more (cell population of Example 1: 99.9% and cell population of Comparative Example 1: 99.8%), and the proportions of STRO-1-negative adherent cells derived from a fetal appendage were 95% or more (cell population of Example 1: 100.0% and cell population of Comparative Example 1: 99.9%).

<Analysis of Gene Expression>

For the adherent cells derived from a fetal appendage of the 6th passage cultured in Comparative Example 1 and Example 1, the expressions of LFA-3 gene, HAPLN1 gene, CCND2 gene, and SDHA gene were analyzed using a microarray analysis.

The microarray was performed by the procedures (1) to (5) described below. Here, the following procedures (3) to (5) were entrusted to and performed by RIKEN GENESIS CO., LTD.

(1) The cell populations of the 6th passage cultured in Comparative Example 1 and Example 1 were dissociated from the plastic culture vessel using a cell scraper (manufactured by Corning Inc.) and recovered by centrifugation.

(2) RNAlater (manufactured by Thermo Fisher Scientific Inc.) was added to the obtained cell pellet to stably store RNA, followed by extraction and purification of total RNA using RNeasy Plus Mini kit (manufactured by QIAGEN ltd.).

(3) From 100 ng of total RNA, cDNA was synthesized by reverse transcription. Then, cDNA was transcribed into cRNA by in vitro transcription and labeled with biotin (using 3'IVT PLUS Reagent Kit).

(4) Labeled cRNA 10.0 mg was added to a hybridization buffer and subjected to hybridization for 16 hours on Human GeneGenome U133A 2.0 Array (manufactured by Affymetrix, Inc.). The hybridized product was washed with GeneChip Fluidics Station 450 (manufactured by Affymetrix, Inc.) and stained with phycoerythrin, followed by being scanned using Gene Chip Scanner 3000 7G (manufactured by Affymetrix, Inc.) and subjected to image analysis with AGCC (Affymetrix GeneChip Command Console Software) (manufactured by Affymetrix, Inc.). The image data was quantified using Affymetrix Expression Console (Manufactured by Affymetrix, Inc.).

(5) The numerical data file was analyzed using analysis software GeneSpring GX (manufactured by Agilent Technologies, Inc.).

The expression level of each gene was determined as the amount of relative expression to the expression level of the SDHA gene. The results are shown in Table 2 below.

TABLE 2

Analysis results of cell characteristics

|  |  | LFA-3 | HAPLN1 | CCND2 |
|---|---|---|---|---|
| Cell population of Example 1 | Fluorescence intensity | 1798.4 | 6327.9 | 343.4 |
|  | Relative expression level* | 1.8 | 6.4 | 0.4 |
| Cell population of Comparative Example 1 | Fluorescence intensity | 790.9 | 573.5 | 4035.3 |
|  | Relative expression level* | 0.8 | 0.5 | 3.8 |

*The relative expression level of each gene to the expression level of SDHA gene From Table 2, it was found that the cell population of Example 1 had a higher relative expression level of LFA-3 gene compared with the cell population of Comparative Example 1. It was found that the relative expression level of LFA-3 gene to the expression level of SDHA gene was 1.0 or more (specifically, 1.8) in the cell population of Example 1 while a relative expression level of LFA-3 gene to the expression level of SDHA gene was less than 1.0 (specifically, 0.8) in the cell population of Comparative Example 1.

From Table 1, it was also found that the cell population of Example 1 had a higher relative expression level of HAPLN1 gene compared with the cell population of Comparative Example 1. It was found that the relative expression level of HAPLN1 gene to the expression level of SDHA gene was 4.0 or more (specifically, 6.4) in the cell population of Example 1 while a relative expression level of HAPLN1 gene to the expression level of SDHA gene was less than 4.0 (specifically, 0.5) in the cell population of Comparative Example 1.

From Table 1, furthermore, it was found that the cell population of Example 1 had a lower relative expression level of CCND2 gene compared with the cell population of Comparative Example 1. It was found that the relative expression level of CCND2 gene to the expression level of SDHA gene was 1.5 or less (specifically, 0.4) in the cell population of Example 1 while the relative expression level of CCND2 gene to the expression level of SDHA gene was higher than 1.5 (specifically, 3.8) in the cell population of Comparative Example 1.

<Evaluation of Differentiation Capacity>

Differentiation capacity was evaluated by procedures (1) to (3) described below.

(1) The cell populations of the 6th passage cultured in Comparative Example 1 and Example 1 were passaged to 12-well plates for adherent culture (Sumitomo Bakelite, Co., Ltd./Product number: MS-80120) and cultured on aMEM (Alpha Modification of Minimum Essential Medium Eagle) containing 10% fetal bovine serum (FBS) (inactivated) and 1× Antibiotic-Antimycotic (manufactured by Thermo Fisher Scientific Inc.) to a confluence of 60% or more and 80% or less.

(2) Using a medium for inducing differentiation into adipocytes (StemPro (registered trademark) Adipogenesis Differentiation Kit, manufactured by Thermo Fisher Scientific Inc.) or a medium for inducing differentiation into chondrocytes (StemPro (registered trademark) Chondrogenesis Differentiation Kit, manufactured by Thermo Fisher Scientific Inc.), the cultivation was carried out for 21 days in an environment at 37° C. with a $CO_2$ concentration of 3% or more and 5% or less. Medium replacement was carried out with a frequency of twice a week.

(3) The cell population cultured using a medium for inducing differentiation into adipocytes was stained with Oil Red O and observed under a microscope. The cell population cultured using a medium for inducing differentiation into chondrocytes was stained with Alcian Blue and observed under a microscope.

The results are shown in FIGS. 5 to 8.

Figure 5:
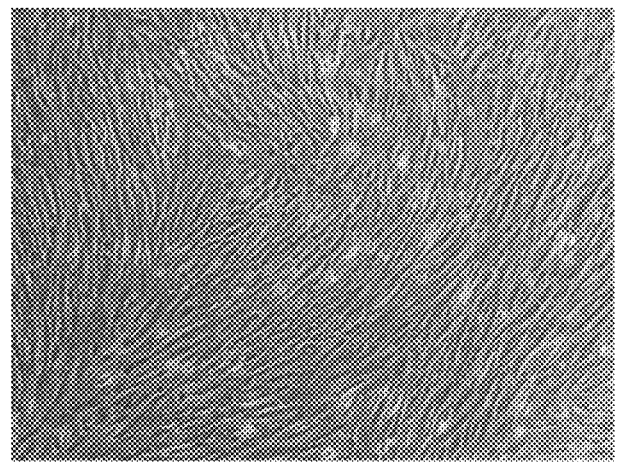
FIG. 5 shows a microscopic image of the adherent cells derived from a fetal appendage cultured in Example 1 which were cultured for 21 days using a medium for inducing differentiation into adipocytes.
Figure 6:
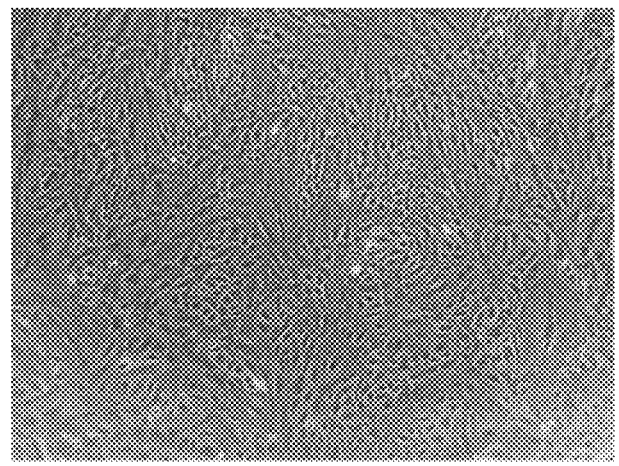
FIG. 6 shows a microscopic image of the adherent cells derived from a fetal appendage cultured in Comparative Example 1 which were cultured for 21 days using a medium for inducing differentiation into adipocytes.

From FIGS. 5 and 6, in the cell population of Comparative Example 1, a large number of rounded cells were observed. Specifically, Oil Red O-stained cells showing mature adipocytes were observed by Oil Red O staining. On the other hand, in the cell population of Example 1, a large number of spindle-shaped cells were observed. Specifically, Oil Red O staining positive cells were not observed. Consequently, it was found that the cell population of Example 1 had a lower differentiation capacity to the adipocytes compared with the cell population of Comparative Example 1.

Figure 7:
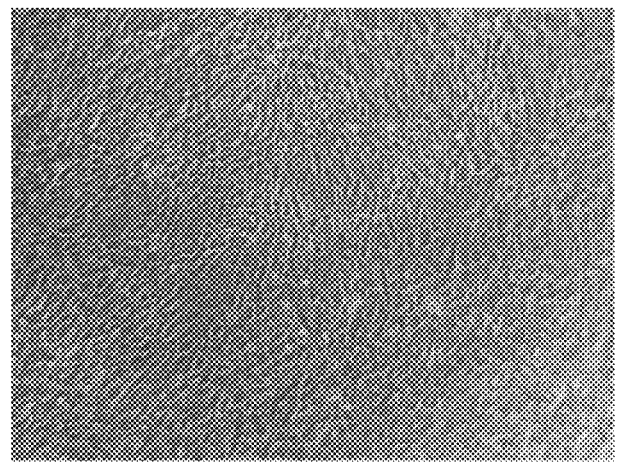
FIG. 7 shows a microscopic image of the adherent cells derived from a fetal appendage cultured in Example 1 which were cultured for 21 days using a medium for inducing differentiation into chondrocytes.
Figure 8:
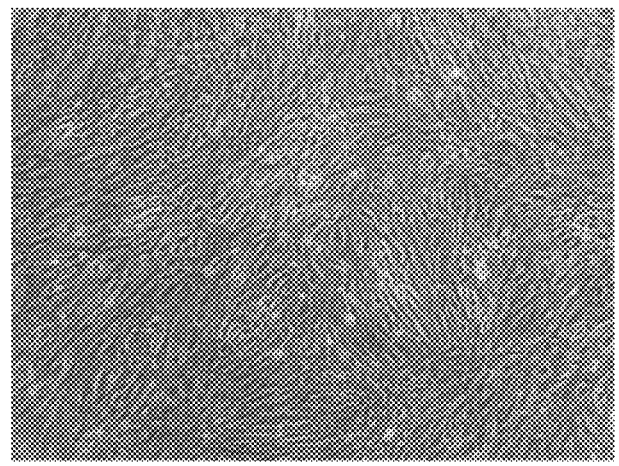
FIG. 8 shows a microscopic image of the adherent cells derived from a fetal appendage cultured in Comparative Example 1 which were cultured for 21 days using a medium for inducing differentiation into chondrocytes.

From FIG. 7 and FIG. 8, no morphological difference was observed in the cell populations of Example 1 and Comparative Example 1, and no accumulation of cartilage-specific extracellular matrix was observed by Alcian Blue staining. Consequently, no differentiation capacity to chondrocytes was observed in any of the cell populations of Example 1 and Comparative Example 1.

Therefore, the cell population having the following cell characteristics (a) and (b) was found to have low differentiation capacity:

(a) in the cell population, the proportion of CD73- and CD90-positive adherent cells derived from a fetal appendage is 90% or more; and (b) the cell population satisfies a relative expression level of LFA-3 gene to the expression level of SDHA gene of 1.0 or more.

The cell population having cell characteristics (a) and (b) shown below was found to have low differentiation capacity:

(a) in the cell population, the proportion of CD73- and CD90-positive adherent cells derived from a fetal appendage is 90% or more; and (b) the cell population satisfies a relative expression level of CCND2 gene to the expression level of SDHA gene of 1.5 or less.

It was suggested that the conditions of the above (a) and (b) were effective as indexes to obtain a cell population having low differentiation capacity. In other words, according to the present invention, the use of the conditions of the above (a) and (b) as indexes make it possible to obtain a cell population comprising adherent cells having low differentiation capacity from a fetal appendage, which can be used for cell preparation. By subjecting the cell population to the production of cell preparation, highly safe cell preparations can be produced with reduced risk of causing ectopic tissue formation.

Example 2

In a manner similar to Example 1, "Step 1: Collection of amnion" from a pregnant woman who was an elective cesarean section case after the obtaining of informed consent (a donor different from Comparative Example 1 and Example 1), "Step 2: Enzyme treatment of amnion and recovery of adherent cells derived from a fetal appendage", "Step 3: Cryopreservation of adherent cells derived from a fetal appendage", and "Step 4: Culture of adherent cells derived from a fetal appendage" were carried out. In the culture of adherent cells derived from a fetal appendage, a portion of the cell population of each passage was collected. Then, each of the collected cell populations were evaluated for the conditions (a) and (b) below. The evaluation of the conditions was carried out using the same procedures as those of the above sections "Analysis of surface antigen expression" and "Analysis of gene expression".

(a) In the cell population, the proportion of CD73- and CD90-positive adherent cells derived from a fetal appendage is 90% or more; and (b) the cell population satisfies a relative expression level of LFA-3 gene to the expression level of SDHA gene of 1.0 or more.

The collected cell populations included those satisfying the above conditions (a) and (b) and those unsatisfying them. Thus, the two different cell populations were evaluated for differentiation capacity using the same procedure as "Evaluation of differentiation capacity" described in paragraph 0133.

As a result, compared with the cell population unsatisfying the conditions (a) and (b), the cell population satisfying the conditions (a) and (b) had low differentiation capacity to adipocytes and no recognizable differentiation capacity to chondrocytes. Since the cell population satisfying the conditions (a) and (b) has low differentiation capacity compared with the cell population unsatisfying the conditions (a) and (b), therefore, the use of the conditions (a) and (b) as an index allows a cell population having low differentiation capacity to be selectively obtained.

Example 3

Production of Pharmaceutical Composition

A portion of the cell population obtained in the above Example 1 is subjected to the preparation of a pharmaceutical composition. A pharmaceutical composition (cell preparation) comprising 20 mL of RPMI1640 medium containing $4.0 \times 10^8$ adherent cells derived from a fetal appendage, 800 mg of HES, 0.7 mL of DMSO, and 800 mg of human serum albumin is prepared. The pharmaceutical composition is enclosed in a bag for freezing and preserved in a frozen state. The pharmaceutical composition can be thawed upon use and applied to a patient.

The invention claimed is:

1. A method for producing an isolated cell population comprising adherent cells derived from a fetal appendage, the method comprising collecting a sample from the fetal appendage; treating the sample comprising an extracellular matrix layer collected from the fetal appendage with an enzyme solution to release adherent cells contained in the extracellular matrix layer;

cryopreserving the adherent cells derived from the fetal appendage to obtain cryopreserved adherent cells;

thawing the cryopreserved adherent cells to obtain thawed adherent cells; and culturing the thawed adherent cells to obtain cultured adherent cells;

isolating from the cultured adherent cells a CD73-positive and CD90-positive cell population having 90% or more of CD73-positive and CD90-postive cells by surface antigen flow cytometry using an antibody corresponding to CD73 antigen and an antibody corresponding to CD90 antigen, measuring a relative expression level of LFA-3 gene to an expression level of SDHA gene in the CD73-positive and CD90-positive cell population by a microarray analysis; and selecting the CD73-positive and CD90-positive cell population having the relative expression level of LFA-3 gene to the expression level of SDHA gene of 1.0 or more to obtain the isolated cell population having the following cell characteristics (a) and (b):

(a) a proportion of CD73-positive and CD90-positive adherent cells derived from the fetal appendage is 90% or more; and (b) the relative expression level of LFA-3 gene to the expression level of SDHA gene is 1.0 or more.

2. The method of claim 1, wherein the enzyme solution comprises a collagenase, a metalloproteinase, or both.

3. The method of claim 1, wherein the cell population has a differentiation capacity that is lower than a differentiation capacity of a cell population that does not have cell characteristics (a) and (b).

4. The method of claim 1, wherein the cryopreserved adherent cells are culturable up to 40 days or more, after start of an in vitro culture of the adherent cells.

* * * * *